US009870505B2

(12) United States Patent
Dante et al.

(10) Patent No.: US 9,870,505 B2
(45) Date of Patent: Jan. 16, 2018

(54) HYPERSPECTRAL IMAGING SYSTEM FOR MONITORING AGRICULTURAL PRODUCTS DURING PROCESSING AND MANUFACTURING

(71) Applicant: ALTRIA CLIENT SERVICES LLC, Richmond, VA (US)

(72) Inventors: Henry M. Dante, Midlothian, VA (US); Samuel Timothy Henry, Midlothian, VA (US); Seetharama C. Deevi, Midlothian, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

(21) Appl. No.: 14/443,986

(22) PCT Filed: Nov. 19, 2013

(86) PCT No.: PCT/US2013/070809
§ 371 (c)(1),
(2) Date: May 19, 2015

(87) PCT Pub. No.: WO2014/078858
PCT Pub. Date: May 22, 2014

(65) Prior Publication Data
US 2015/0347815 A1  Dec. 3, 2015

Related U.S. Application Data

(60) Provisional application No. 61/728,123, filed on Nov. 19, 2012.

(51) Int. Cl.
*G06K 9/00* (2006.01)
*G01J 3/28* (2006.01)
(Continued)

(52) U.S. Cl.
CPC .............. *G06K 9/0063* (2013.01); *A24B 3/16* (2013.01); *A24B 15/18* (2013.01); *B07C 5/342* (2013.01);
(Continued)

(58) Field of Classification Search
CPC .... A24B 15/18; A24B 3/16; G01J 2003/2826; G01J 3/28; G01N 2021/8466;
(Continued)

(56) References Cited

U.S. PATENT DOCUMENTS 3,854,586 A    12/1974  Perkins, III
3,939,983 A     2/1976  Asfour
(Continued)

FOREIGN PATENT DOCUMENTS

CN       101627832 A     1/2010
WO       00/58035 A1    10/2000
(Continued)

OTHER PUBLICATIONS

International Search Report of International Application No. PCT/US2013/070809 dated Mar. 7, 2014.
(Continued)

*Primary Examiner* — Bhavesh Mehta
*Assistant Examiner* — Ian Lemieux
(74) *Attorney, Agent, or Firm* — Roberts Mlotkowski Safran Cole & Calderon, P.C.

(57) ABSTRACT

Provided is a method for monitoring a manufacturing process of an agricultural product. The method utilizes hyperspectral imaging and comprises scanning at least one region along a sample of agricultural product using at least one light source of a single or different wavelengths; generating hyperspectral images from the at least one region; determining a spectral fingerprint for the sample of agricultural product from the hyperspectral images; and comparing the
(Continued)

spectral fingerprint so obtained to a spectral fingerprint database containing a plurality of fingerprints obtained at various points of the manufacturing process, using a computer processor, to determine which point in the manufacturing process the sample has progressed to.

31 Claims, 8 Drawing Sheets

(51) Int. Cl.
A24B 15/18 (2006.01)
G06K 9/62 (2006.01)
G06K 9/46 (2006.01)
G01N 21/31 (2006.01)
A24B 3/16 (2006.01)
B07C 5/342 (2006.01)
B07C 5/36 (2006.01)
G06F 17/30 (2006.01)
G06T 7/00 (2017.01)
G01N 21/84 (2006.01)

(52) U.S. Cl.
CPC ............... B07C 5/366 (2013.01); G01J 3/28 (2013.01); G01J 3/2823 (2013.01); G01N 21/31 (2013.01); G01N 21/84 (2013.01); G06F 17/3028 (2013.01); G06K 9/4604 (2013.01); G06K 9/6202 (2013.01); G06T 7/0008 (2013.01); G01J 2003/2826 (2013.01); G01N 2021/8461 (2013.01); G01N 2021/8466 (2013.01); G06K 2009/4657 (2013.01); G06T 2207/20024 (2013.01); G06T 2207/30108 (2013.01); G06T 2207/30188 (2013.01)

(58) Field of Classification Search
CPC .................. G01N 21/31; G01N 21/84; G06K 2009/4657; G06K 9/0063; G06T 2207/30188
See application file for complete search history.

(56) References Cited

U.S. PATENT DOCUMENTS

| | | | |
|---|---|---|---|
| 4,018,674 A | 4/1977 | Morris | |
| 4,528,993 A | 7/1985 | Sensabaugh et al. | |
| 4,609,108 A | 9/1986 | Hristozov et al. | |
| 4,624,269 A | 11/1986 | Story et al. | |
| 4,778,987 A | 10/1988 | Saaski et al. | |
| 4,836,224 A | 6/1989 | Lawson et al. | |
| 4,924,883 A | 5/1990 | Perfetti et al. | |
| 4,924,888 A | 5/1990 | Perfetti et al. | |
| 4,987,907 A | 1/1991 | Townend | |
| 5,056,537 A | 10/1991 | Brown et al. | |
| 5,085,325 A | 2/1992 | Jones et al. | |
| 5,092,352 A | 3/1992 | Sprinkle | |
| 5,159,942 A | 11/1992 | Brinkley et al. | |
| 5,220,930 A | 6/1993 | Gentry | |
| 5,301,694 A | 4/1994 | Raymond et al. | |
| 5,360,023 A | 11/1994 | Blakley et al. | |
| 5,387,416 A | 2/1995 | White | |
| 5,476,108 A | 12/1995 | Dominguez et al. | |
| 5,972,404 A | 10/1999 | van Lengerich | |
| 6,400,833 B1 | 6/2002 | Richert | |
| 6,421,126 B1 | 7/2002 | Kida et al. | |
| 6,587,575 B1* | 7/2003 | Windham | G01N 21/31 250/458.1 |
| 6,646,264 B1 | 11/2003 | Modiano et al. | |
| 6,701,936 B2 | 3/2004 | Shafer et al. | |
| 6,730,832 B1 | 5/2004 | Dominguez et al. | |
| 6,819,798 B2 | 11/2004 | Gorin | |
| 6,953,040 B2 | 10/2005 | Atchley et al. | |
| 7,032,601 B2 | 4/2006 | Atchley et al. | |
| 7,142,988 B1 | 11/2006 | Johnson | |
| 7,335,847 B2 | 2/2008 | Drewes et al. | |
| 7,383,840 B2 | 6/2008 | Coleman | |
| 7,411,682 B2 | 8/2008 | Moshe | |
| 7,450,761 B2 | 11/2008 | Portigal et al. | |
| 7,518,710 B2 | 4/2009 | Gao et al. | |
| 8,564,769 B2 | 10/2013 | Zou et al. | |
| 8,775,219 B2 | 7/2014 | Swanson et al. | |
| 8,953,158 B2 | 2/2015 | Moshe et al. | |
| 8,967,851 B1 | 3/2015 | Kemeny | |
| 2001/0000386 A1 | 4/2001 | Peele | |
| 2002/0008055 A1 | 1/2002 | Campbell et al. | |
| 2003/0075193 A1 | 4/2003 | Li et al. | |
| 2003/0131859 A1 | 7/2003 | Li et al. | |
| 2004/0084056 A1 | 5/2004 | Lawson et al. | |
| 2004/0255965 A1 | 12/2004 | Perfetti et al. | |
| 2005/0057263 A1 | 3/2005 | Moshe et al. | |
| 2005/0066984 A1 | 3/2005 | Crooks et al. | |
| 2005/0066986 A1 | 3/2005 | Nestor et al. | |
| 2005/0244521 A1 | 11/2005 | Strickland et al. | |
| 2006/0292246 A1 | 12/2006 | Wu et al. | |
| 2009/0171591 A1* | 7/2009 | Timmis | G01J 3/02 702/19 |
| 2009/0293889 A1 | 12/2009 | Kumar et al. | |
| 2011/0125477 A1 | 5/2011 | Lightner et al. | |
| 2012/0250025 A1 | 10/2012 | Moshe et al. | |
| 2012/0321759 A1 | 12/2012 | Marinkovich et al. | |
| 2013/0022250 A1 | 1/2013 | Nygaard et al. | |
| 2015/0044098 A1 | 2/2015 | Smart et al. | |
| 2015/0283586 A1 | 10/2015 | Dante et al. | |

FOREIGN PATENT DOCUMENTS

| | | |
|---|---|---|
| WO | 02/37990 A2 | 5/2002 |
| WO | 2004/095959 A1 | 11/2004 |
| WO | 2005/016036 A1 | 2/2005 |
| WO | 2005/041699 A2 | 5/2005 |
| WO | 2005/063060 A1 | 7/2005 |
| WO | 2007041755 A1 | 4/2007 |
| WO | 2007/099540 A2 | 9/2007 |
| WO | 2011/027315 A1 | 3/2011 |
| WO | 2014/078858 A1 | 5/2014 |
| WO | 2014/078861 A1 | 5/2014 |
| WO | 2014/078862 A1 | 5/2014 |

OTHER PUBLICATIONS

Pilar Beatriz Garice-Allende, "Hyperspectral Imaging Sustains Production-Process Competitiveness", Spie Newsroom, Jan. 1, 2010, DOI:10.11172.1201003.002681.
Timothy Kelman et al., "Classification of Chinese Tea Samples for Food Quality Control Using Hyperspectral Imaging", Hyperspectral Imaging Conference, Jan. 1, 2011.
International Search Report of International Application No. PCT/US2013/070812 dated Mar. 7, 2014.
Robin Gruna et al., "Hyperspectral Imaging—From Laboratory to In-line Food Sorting", Cigar Workshop on Image Analysis in Agriculture, Jan. 1, 2010.
Luis Rodriguez-Cobo et al., "Raw Material Classification by Means of Hyperspectral Imaging and Hierarchical Temporal Memories", IEEE Sensors Journal, IEEE Service Center, New York, NY, US, vol. 12, No. 9, Sep. 1, 2012, ISSN:1530-437X, DOI: 10.1109.2012.2202898.
P. Beatriz Garcia-Allende et al., "Hyperspectral Imaging for Diagnosis and Quality Control in Agri-food and Industrial Sectors, "Proceedings of SPIE:,vol. 7726, Apr. 30, 2011, ISSN: 0277-786X,DOI: 10.1117.12.744506.
International Search Report of International Application No. PCT/US2013/070814 dated Mar. 7, 2014.
Russ Ouellette, "The Basics of Tobacco and Blending", pipesmagaazine.com, Jul. 14, 2010, Retrieved from the Internet: URL: http://pipesmagazine.com/blog/put-that-in-your-pipe/the-basucs-of-tobacco-blending.
Browne, "The Design of Cigarettes", 3.sup.rd Ed., pp. 43 (1990).
International Preliminary Report on Patentability of PCT/IB2010/053952 dated Mar. 6, 2012.

(56) References Cited

OTHER PUBLICATIONS

International Preliminary Report on Patentability of PCT/US2013/070809 dated May 19, 2015.
International Preliminary Report on Patentability of PCT/US2013/070812 dated May 19, 2015.
International Preliminary Report on Patentability of PCT/US2013/070814 dated May 19, 2015.
Garner, "Principles and Practical Methods of Curing Tobacco", USDA Bulletin No. 143, 7-54 (1909).
Darkis et al., "Flue-Cured Tobacco Correlation between Chemical Compositio and Stalk Position of Tobaccos Produced under Varying Weather Conditions", Industrial & Engineering Chemistry, 28 (10) 1214-1223 (1936).
Bacon et al., "Biochemical Changes in Tobacco During Flue Curing", USDA Tech. Bulletin No. 1032 (1951).
Darkis et al., "Cigarette Tobaccos. Chemical Changes that Occur during Processing" Industrial & Engineering , chemistry, 44 (2), 284-291 (1952).
Bacon et al., "Chemical Changes in Tobacco during Flue-Curing", Industrial & Engineering Chemistry, 44 (2), 292-309 1952).
Walker et al., "Curing Flue-Cured Tobacco in Canada", Publication 1312/E (1987).
Suggs et al., "Bulk Density and Drying Effect on Air Flow Through Flue-Cured Tobacco Leaves", Tobacco Scence yearbook, 33, 86-90 (1989).
Hawks, Jr., "Principles of Flue-Cured Tobacco Production", Second Edition (1978).
"Flue-Cured Tobacco Information", North Carolina Cooperative Extension Service, North Carolina State University, 1993.
Peele et al., "Impact of Plant Manipulation and Post Harvest Phenomena on Leaf Composition", Recent Advances in Tobacco Science, 21, 1-181 (1995).
Cooper et al., "Drying and Curing of Bright Leaf Tobacco by Means of Conditioned Air: Engineering Experiment Station Series" Bulletin of the Virginia Polytechnic Institute, 37(6), 3-28 (1939).
Brown et al., "Engineering Phases of Curing Bright Leaf Tobacco", Agriculture Engineering, 29(3), 109-111 (1948).
Johnson et al., "Bulk Curing of Bright Leaf Tobacco", Tobacco Science, 4, 49-55 (1960).
Johnson, "Production factors affecting chemical properties of the flue-cured leaf", Tobacco International 177(11): 12-19 (1975).
Davis et al., "Tobacco: Production, Chemistry and Technology", 1st Edition, pp. 131-133 (1999).
Legg et al., "40th Tobacco Chemists' Research Conference", Holiday Inn World's Fair (1986).
Davis et al., "Tobacco Production, Chemistry and Technology", Blackwell Science, pp. 346 and 440-451, (1999).
Voges, "Tobacco Encyclopedia", Tobacco Journal International, pp. 44-45 (1984).
Bombick et al. "Evaluation of the Genotoxic and Cytotoxic Potential of Mainstream Whole Smoke and Smoke Condensate from a Cigarette Containing a Novel Carbon Filter", Fundamental and Applied Toxicology, vol. 39, pp. 11-17 (1997).

\* cited by examiner

HYPERSPECTRAL IMAGING SYSTEM FOR MONITORING AGRICULTURAL PRODUCTS DURING PROCESSING AND MANUFACTURING

FIELD

Disclosed herein is a method and system for monitoring the processing of agricultural products, such as tobacco, using hyperspectral imaging and analysis. Embodiments disclosed herein can be practiced with other agricultural products, including but not limited to, tea, grapes, coffee, vegetables, fruit, nuts, breads, cereals, meat, fish and other plant or animal parts.

ENVIRONMENT

Certain agricultural products, such as cultivated tobacco plants tea, spinach, etc., are harvested for their leaves, which may then be dried and cured as in the case of tobacco or tea. In the manufacture of cigarettes and other tobacco products, different types of tobaccos are frequently processed, with three main types of tobacco used in U.S. blends. These tobacco types are Virginia or flue-cured, Burley and Oriental. In the following, the method and the system disclosed herein are illustrated for application in the tobacco industry, though the same method and system could be used for other agricultural products using leaves like tea and spinach, or in other packaged agricultural products using fruits, grapes, tomatoes, and other vegetables.

Tobacco, in many cases, contain tobacco materials that have processed forms, such as processed tobacco stems (e.g., cut-rolled stems, cut-rolled-expanded stems or cut-puffed stems), volume expanded tobacco (e.g., puffed tobacco, such as dry ice expanded tobacco (DIET), preferably in cut filler form). Tobacco materials also can have the form of reconstituted tobaccos (e.g., reconstituted tobaccos manufactured using paper-making type or cast sheet type processes). Tobacco reconstitution processes traditionally convert portions of tobacco that normally might otherwise be treated as waste, into commercially useful forms. For example, tobacco stems, recyclable pieces of tobacco and tobacco dust can be used to manufacture processed reconstituted tobaccos of fairly uniform consistency. See, for example, Tobacco Encyclopedia, Voges (Ed.) p. 44-45 (1984), Browne, The Design of Cigarettes, 3.sup.rd Ed., p. 43 (1990) and Tobacco Production, Chemistry and Technology, Davis et al. (Eds.) p. 346 (1999).

Various representative tobacco types, processed types of tobaccos, types of tobacco blends, cigarette components and ingredients, and tobacco rod configurations, also are set forth in U.S. Pat. No. 4,836,224 to Lawson et al.; U.S. Pat. No. 4,924,883 to Perfetti et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,730,832 to Dominguez et al.; and U.S. Pat. No. 6,701,936 to Shafer et al.; U.S. Patent Application Publication Nos. 2003/0075193 to Li et al.; 2003/0131859 to Li et al.; 2004/0084056 to Lawson et al.; 2004/0255965 to Perfetti et al.; 2005/0066984 to Crooks et al.; and 2005/0066986 to Nestor et al.; PCT WO 02/37990 to Bereman; and Bombick et al., Fund. Appl. Toxicol., 39, p. 11-17 (1997); which are incorporated herein by reference.

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are set forth in U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; U.S. Pat. Appl. Pub. Nos. 2005/0244521 to Strickland et al.; and 2009/0293889 to Kumar et al.; PCT Pat. App. Publ. WO04/095959 to Arnarp et al.; PCT Pat. App. Publ. WO05/063060 to Atchley et al.; PCT Pat. App. Publ. WO05/016036 to Bjorkholm; and PCT Pat. App. Publ. WO05/041699 to Quinter et al., each of which is incorporated herein by reference. See, for example, the types of smokeless tobacco formulations, ingredients, and processing methodologies set forth in U.S. Pat. No. 6,953,040 to Atchley et al. and U.S. Pat. No. 7,032,601 to Atchley et al., each of which is incorporated herein by reference.

Dark air-cured tobacco is a type of tobacco used mainly for chewing tobacco, snuff, cigars, and pipe blends. Most of the world production of such tobacco is confined to the tropics; however, sources of dark air-cured tobacco are also found in Kentucky, Tennessee, and Virginia. Dark air-cured tobacco plants are characterized by leaves with a relatively heavy body and such tobacco plants are typically highly fertilized and topped low to around 10-12 leaves. See Tobacco Production, Chemistry and Technology, Davis et al. (Eds.) pp. 440-451 (1999).

The manner in which various tobacco varieties are grown, harvested and processed is well known. See, Garner, USDA Bulletin No. 143, 7-54 (1909); Darkis et al, Ind. Eng. Chem., 28, 1214-1223 (1936); Bacon et al., USDA Tech. Bulletin No. 1032 (1951); Darkis et al., Ind. Eng. Chem., 44, 284-291 (1952); Bacon et al., Ind. Eng. Chem., 44, 292-309 (1952); Curing Flue-Cured Tobacco in Canada, Publication 1312/E (1987); and Suggs et al., Tob. Sci., 33, 86-90 (1989). See, also, Hawks, Jr., Principles of Flue-Cured Tobacco Production, 2.sup.Ed. (1978); Flue-Cured Tobacco Information 1993, N. C. Coop. Ext. Serv.; and Peele et al., Rec. Adv. Tob. Sci., 21, 81-123 (1995). Those references are incorporated herein by reference. In general, harvesting includes disrupting the senescence process by removing tobacco leaves from the plant at a desirable point in the plant life cycle.

It has been common practice to flue-cure certain tobaccos, such as Virginia tobaccos, in barns using a so-called flue-curing process. Cooper et al., VPI Bull., 37(6), 3-28 (1939); Brown et al., Agric. Eng., 29(3), 109-111 (1948); Johnson et al., Job. Sci., 4, 49-55 (1960); Johnson, Rec. Adv. Tob. Sci., Inag. Vol., 63-78 (1974); Peele et al., Rec. Adv. Job. Sci., 21, 81-123 (1995). Tobacco to be cured may be grown under well-known and accepted agronomic conditions, and harvested using known techniques. Such tobacco typically is referred to as green tobacco. Most preferably, the harvested tobacco is adequately ripe or mature. Peele et al., Rec. Adv. Tob. Sci., 21, 81-123 (1995). Ripe or mature tobaccos typically require shorter cure times than do unripe or immature tobaccos.

Under typical conditions green tobacco is placed in an enclosure adapted for curing tobacco, commonly referred to in the art as a curing barn. The tobacco will be subjected to curing conditions, typically involving the application of heat. The green tobacco can be placed in the barn in a variety of ways, and typically is carried out as a manner of personal preference. As such, there is wide discretion in the particular determination of the amount of tobacco placed within the barn, the packing density of that tobacco within a box, the spacing of the tobacco within the barn, and the location of various tobacco samples within the barn. See, for example, U.S. Pat. App. Pub. 2001/0386 to Peele and Tobacco Production, Chemistry and Technology, Davis et al. (Eds.) p. 131-133 (1999). Fire-curing, air-curing, sun-curing, and other curing processes are also known in the art.

The conditions of temperature to which the tobacco is exposed during curing can vary. The time frame over which curing of the tobacco occurs also can vary. For the flue-curing of Virginia tobaccos, the temperature to which the tobacco is exposed typically is in the range of about 35° C. to about 75° C.; and the time over which the tobacco is exposed to those elevated temperatures usually is at least about 120 hours, but usually is less than about 200 hours. Curing temperatures reported herein generally are representative of the average air temperature within the curing barn during curing process steps. Average air temperatures can be taken at one or more points or locations within the curing barn that give an accurate indication of the temperature that the tobacco experiences during curing steps. Typically, Virginia tobacco first is subjected to a yellowing treatment step whereby the tobacco is heated at about 35° C. to about 40° C. for about 24 to about 72 hours, preferably about 36 to about 60 hours; then is subjected to a leaf drying treatment step whereby the tobacco is heated at about 40° C. to about 57° C. for about 48 hours; and then is subjected to a midrib (i.e., stem) drying treatment step whereby the tobacco is heated at about 57° C. to about 75° C. for about 48 hours. Exposing Virginia tobacco to temperatures above about 70° C. to about 75° C. during curing is not desirable, as exposure of the tobacco to exceedingly high temperatures, even for short periods of time, can have the effect of decreasing the quality of the cured tobacco. Typically, some ambient air preferably is introduced into the barn during the yellowing stage, significantly more ambient air preferably is introduced into the barn during the leaf drying stage, and heated air preferably is recirculated within the barn during midrib drying stage. The relative humidity within the barn during curing varies, and is observed to change during curing. Typically, a relative humidity of about 85 percent is maintained within the curing barn during the yellowing stage, but then is observed to decrease steadily during leaf drying and midrib drying stages. Of course, fire curing and air curing each provide different conditions of temperature, humidity, and times for various curing steps.

After the tobacco is exposed to curing conditions, the use of heating is stopped. Typically, the fresh air dampers of the barn are opened in order to allow contact of ambient air with that tobacco. As such, moisture within the ambient air is allowed to moisten the tobacco; and the very dry freshly cured tobacco is rendered less brittle. The cooled tobacco then is taken down, and the tobacco is removed from the curing barn. Commonly, fire-cured tobaccos for oral-use tobacco are stored and aged for at least three years after curing is complete, during which time anaerobic fermentation occurs. After this, period of anaerobic fermentation storage, the aged tobacco undergoes 5 to 8 weeks of aerobic fermentation in preparation for use in modern moist snuff products, which generally reduces the presence of bitterness-causing compounds in the tobacco. The long time taken for this traditional curing and aging process incurs expenses and delays in production of oral-use/smokeless tobacco.

It has been known practice to cure certain types of tobaccos, particularly specialty tobaccos, using a so-called fire-curing process. Legg et al., TCRC (1986). It also has been common practice to flue-cure certain tobaccos, such as Virginia tobaccos, in barns using a so-called flue-curing process, one general description of which is included above. See also Cooper et al., VPI Bull., 37(6), 3-28 (1939); Brown et al., Agric. Eng., 29(3), 109-111 (1948); Johnson et al., Tob. Sci., 4, 49-55 (1960); Peele et al., Rec. Adv. Tob. Sci., 21, 81-123 (1995). Tobacco leaf is harvested, placed in barns, and subjected to the application of heat. In recent years, it has been common practice, particularly in North America, to cure tobacco using a so-called direct-fire curing technique. Typical direct-fire heating units are powered by propane, and during use, those heating units produce exhaust gases that come into contact with the tobacco being cured.

One type of smokeless tobacco product is referred to as "snuff." Representative types of moist snuff products, including those types commonly referred to as "snus," have been manufactured in Europe, particularly in Sweden, by or through companies such as Swedish Match AB, Fiedler & Lundgren AB, Gustavus AB, Skandinavisk Tobakskompagni NS, and Rocker Production AB. Exemplary smokeless tobacco products that have been marketed include those referred to as CAMEL Snus, CAMEL Orbs, CAMEL Strips and CAMEL Sticks by R. J. Reynolds Tobacco Company; GRIZZLY moist tobacco, KODIAK moist tobacco, LEVI GARRETT loose tobacco and TAYLOR' PRIDE loose tobacco by American Snuff Company, LLC; KAYAK moist snuff and CHATTANOOGA CHEW chewing tobacco by Swisher International, Inc.; REDMAN chewing tobacco by Pinkerton Tobacco Co. LP; COPENHAGEN moist tobacco, COPENHAGEN Pouches, SKOAL Bandits, SKOAL Pouches, RED SEAL long cut and REVEL Mint Tobacco Packs by U.S. Smokeless Tobacco Company; and MARLBORO Snus and Taboka by Philip Morris USA. Representative smokeless tobacco products also have been marketed under the tradenames Oliver Twist by House of Oliver Twist A/S. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard.

As in the case of any agricultural product, tobacco may be characterized by a wide variety of physical, chemical, and/or biological properties, characteristics, features, and behavior, which are associated with various aspects relating to agriculture, agronomy, horticulture, botany, environment, geography, climate, and ecology of the tobacco crop and plants thereof from which tobacco leaves are derived, as well as the manner in which the tobacco has been processed, aged or fermented to produce the sensorial characteristics sought to be achieved by such further processing. Moreover, as those skilled in the art will plainly recognize, these characteristics can vary in time throughout further processing, aging or fermentation.

In summary, the types of processes and times involved in processing tobacco for curing vary, and include air curing, flue curing, fire curing, and other curing processes. It would be desirable to provide a system and method for monitoring and optimizing these manufacturing processes which alter the character and nature of tobacco useful in the manufacture of tobacco products. Likewise, it would be desirable to provide a system and method for monitoring and optimizing the manufacturing processes of other agricultural products, including, but not limited to, tea, spinach, fruits, vegetables, etc.

In the general technique of hyperspectral imaging, one or more objects in a scene or sample are affected in a way, such as excitation by incident electromagnetic radiation supplied by an external source of electromagnetic radiation upon the objects, which causes each object to reflect, scatter and/or emit electromagnetic radiation featuring a spectrum.

Hyperspectral imaging and analysis is a combined spectroscopy and imaging type of analytical method involving the sciences and technologies of spectroscopy and imaging. By definition, hyperspectral imaging and analysis is based on a combination of spectroscopy and imaging theories, which are exploitable for analyzing samples of physical, chemical, and/or biological matter in a highly unique, specialized, and sophisticated, manner.

Hyperspectral images generated by and collected from a sample of matter may be processed and analyzed by using automatic pattern recognition and/or classification type data and information processing and analysis, for identifying, characterizing, and/or classifying, the physical, chemical, and/or biological properties of the hyperspectrally imaged objects in the sample of matter.

There remains a need for a method and system for monitoring and optimizing the manufacturing processes of agricultural products, such as tobacco, via hyperspectral imaging and analysis.

SUMMARY

Disclosed herein is a method and system for monitoring and optimizing the manufacturing processes of agricultural products, including tobacco, via hyperspectral imaging and analysis. The method and system disclosed herein provide high sensitivity, high resolution, and high speed operation, in a simple yet highly efficient, cost effective and commercially applicable manner.

In one aspect, disclosed herein is a method for monitoring the manufacturing of an agricultural product, the method utilizing hyperspectral imaging and comprising: scanning at least one region along a sample of agricultural product using at least one light source of a single or different wavelengths; generating hyperspectral images from the at least one region; determining a spectral fingerprint for the sample of agricultural product from the hyperspectral images; and comparing the spectral fingerprint so obtained to a spectral fingerprint database containing a plurality of fingerprints obtained at various points of the manufacturing process, using a computer processor, to determine which point in the manufacturing process the sample has progressed to.

In one form, a method is provided to monitor a manufacturing process based upon obtaining hyperspectral signatures for the agricultural material being processed, thus minimizing or eliminating the need for human evaluation. To accomplish this, first a standard database is created that includes hyperspectral signatures taken at each step of a process, such as a tobacco aging or fermentation process. The database so obtained is used as a benchmark against which the process will be monitored at each step of the process. Adjustments can them be made to the process on a real-time basis, by controlling the processing parameters to ensure the quality of the final product.

In one form, a spectral fingerprint is formed for the sample from the hyperspectral images. One or more features of the spectral fingerprint are correlated to desirable sensory attributes of the sample. A wide variety of physical, chemical, and/or biological properties may be determined. Certain forms disclosed herein may be performed in an automatic on-line manner, via hyperspectral imaging and analysis.

In another form, the method includes scanning multiple regions along the sample of agricultural product using at least one light source of a single or different wavelengths; and generating hyperspectral images from the multiple regions.

In another form, the method includes determining a physicochemical code for the sample.

In still yet another form, the method includes the object of the manufacturing process is to obtain an agricultural product with desirable sensory attributes. In a further form, the method includes determining one or more features of a spectral fingerprint that corresponds to the desirable sensory attributes.

In a yet further form, the agricultural product is tobacco and the manufacturing process is a fermentation process. In a still yet further form, the method determines the time required to complete the fermentation process for the tobacco sample.

In one form, the agricultural product is tobacco and the manufacturing process is a tobacco aging process. In another form, the method determines the time required to complete the tobacco aging process for the tobacco sample.

In yet another form, the method includes correlating one or more features of the spectral fingerprint of the sample of the agricultural product to the desirable sensory attributes.

In still yet another form, the at least one light source is positioned to minimize the angle of incidence of each beam of light with the sample, the at least one light source including a light source selected from the group consisting of a tungsten light source, a halogen light source, a xenon light source, a mercury light source, an ultraviolet light source, and combinations thereof.

In a further form, manufacturing cost is a factor used by the computer processor.

In a still further form, method further includes storing data about the spectral fingerprints of the plurality of samples of agricultural product within a computer storage means; and storing at least a portion of at least some of the plurality of samples of agricultural product.

In another aspect, provided is a system for monitoring the manufacturing of an agricultural product.

In yet another aspect, provided is a method for determining the stage of processing for an agricultural product, the method utilizing hyperspectral imaging and comprising: (a) scanning multiple regions along a sample of a desirable agricultural product using at least one light source of different wavelengths; (b) generating hyperspectral images from the multiple regions; (c) forming a spectral fingerprint for the sample from the hyperspectral images; and (d) correlating the spectral fingerprint obtained in step (c) to a spectral fingerprint database containing a plurality of fingerprints obtained at various points of processing, using a computer processor, to determine the stage processing.

In one form, the method includes (e) storing data about the spectral fingerprint within a computer storage means; and (f) repeating steps (a), (b), (c), and (d) using a plurality of samples.

In still yet another aspect, provided is a system for determining the stage of processing for an agricultural product.

In a further aspect, provided is a method of determining the stage of processing for a product, the method comprising: resolving whether a sample meets a desired attribute for the product and if so, applying hyperspectral imaging analysis and theoretic analysis to establish a relationship P comprising unique spectra of the sample, said unique spectra comprising at least two spectral elements x and y and values thereof; establishing through hyperspectral imaging analysis a characterization of the sample according to said spectral elements (at least x and y) of said unique spectra P; and mathematically resolving from said characterizations to determine whether the sample achieves the values of said spectral elements of P.

In a still further aspect, provided is a method for controlling a manufacturing process for producing an agricultural product. The method utilizes hyperspectral imaging and comprises obtaining a sample of agricultural product undergoing a manufacturing process, the manufacturing process conducted at one or more predetermined process parameters; scanning at least one region along the sample of agricultural product using at least one light source of a single or different wavelengths; generating hyperspectral images from the at least one region; determining a spectral fingerprint for the sample of agricultural product from the hyperspectral images; comparing the spectral fingerprint obtained in step (c) to a spectral fingerprint database containing a plurality of fingerprints obtained at various points of the manufacturing process, using a computer processor, to determine the stage of processing; and adjusting at least one process parameter to optimize the manufacturing process.

In a still yet further aspect, provided is a method of creating a database for controlling a manufacturing process for producing an agricultural product. The method utilizes hyperspectral imaging and includes the steps of (a) obtaining a dark image and a reference image for calibration; (b) analyzing the reference image to obtain calibration coefficients; (c) obtaining a hyperspectral image for an agricultural sample; (d) removing dark values and normalizing the agricultural sample image; (e) applying calibration coefficients to compensate for fluctuations in system operating conditions; (f) repeating steps (c)-(e) for all agricultural samples; and (g) storing all hyperspectral sample hypercubes to form the database.

In one form, the computer database is stored in a computer readable medium.

Certain forms disclosed herein are implemented by performing steps or procedures, and sub-steps or sub-procedures, in a manner selected from the group consisting of manually, semi-automatically, fully automatically, and combinations thereof, involving use and operation of system units, system sub-units, devices, assemblies, sub-assemblies, mechanisms, structures, components, and elements, and, peripheral equipment, utilities, accessories, and materials. Moreover, according to actual steps or procedures, sub-steps or sub-procedures, system units, system sub-units, devices, assemblies, sub-assemblies, mechanisms, structures, components, and elements, and, peripheral equipment, utilities, accessories, and materials, used for implementing a particular form, the steps or procedures, and sub-steps or sub-procedures are performed by using hardware, software, and/or an integrated combination thereof, and the system units, sub-units, devices, assemblies, sub-assemblies, mechanisms, structures, components, and elements, and peripheral equipment, utilities, accessories, and materials, operate by using hardware, software, and/or an integrated combination thereof.

For example, software used, via an operating system, for implementing certain forms disclosed herein can include operatively interfaced, integrated, connected, and/or functioning written and/or printed data, in the form of software programs, software routines, software subroutines, software symbolic languages, software code, software instructions or protocols, software algorithms, or a combination thereof. For example, hardware used for implementing certain forms disclosed herein can include operatively interfaced, integrated, connected, and/or functioning electrical, electronic and/or electromechanical system units, sub-units, devices, assemblies, sub-assemblies, mechanisms, structures, components, and elements, and, peripheral equipment, utilities, accessories, and materials, which may include one or more computer chips, integrated circuits, electronic circuits, electronic sub-circuits, hard-wired electrical circuits, or a combination thereof, involving digital and/or analog operations. Certain forms disclosed herein can be implemented by using an integrated combination of the just described exemplary software and hardware.

In certain forms disclosed herein, steps or procedures, and sub-steps or sub-procedures can be performed by a data processor, such as a computing platform, for executing a plurality of instructions. Optionally, the data processor includes volatile memory for storing instructions and/or data, and/or includes non-volatile storage, for example, a magnetic hard-disk and/or removable media, for storing instructions and/or data. Optionally, certain forms disclosed herein include a network connection. Optionally, certain forms disclosed herein include a display device and a user input device, such as a touch screen device, keyboard and/or mouse.

BRIEF DESCRIPTION OF THE DRAWINGS

The forms disclosed herein are illustrated by way of example, and not by way of limitation, for the case of processing tobacco for use in manufactured tobacco products in the figures of the accompanying drawings and in which like reference numerals refer to similar elements and in which.

DETAILED DESCRIPTION

Figure 1:
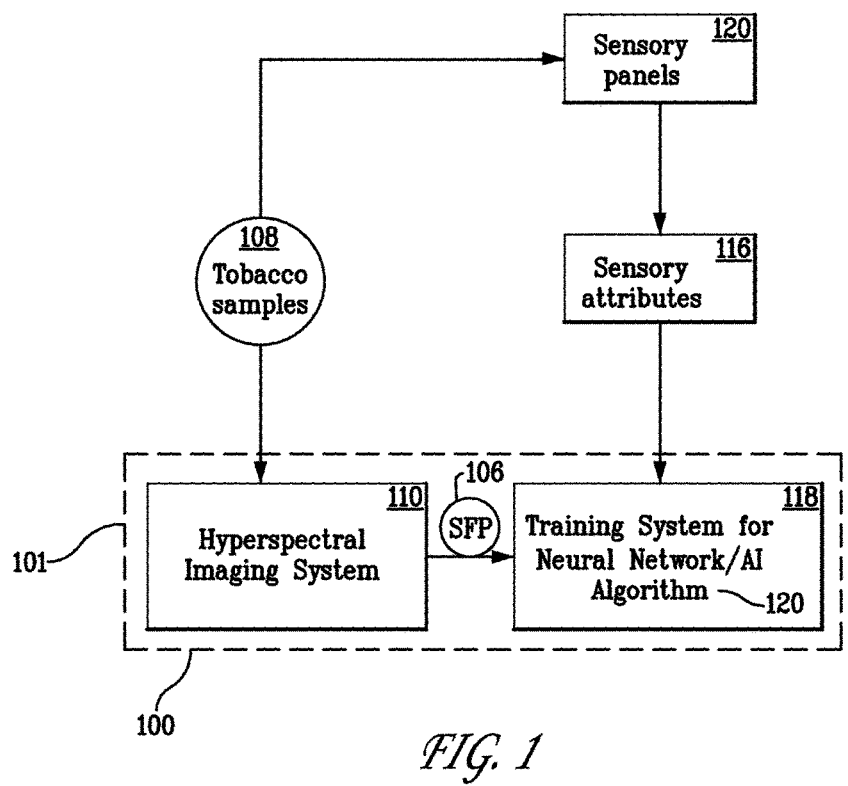
FIG. 1 presents, in block diagram form, a first stage of a system for monitoring the manufacturing of an agricultural product, in accordance herewith.

Various aspects will now be described with reference to specific forms selected for purposes of illustration. It will be appreciated by those skilled in the art that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-8, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways, as can be appreciated by those skilled in the art.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Moreover, all technical and scientific words, terms, and/or phrases, introduced, defined, described, and/or exemplified, in the above sections, are equally or similarly applicable in the illustrative description, examples and appended claims.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, and materials, as well as operation and implementation, of exemplary forms, alternative forms, specific configurations, and, additional and optional aspects, characteristics, or features, thereof, of the methods, and of the systems, disclosed herein, are better understood with reference to the following illustrative description and accompanying drawings. Throughout the following illustrative description and accompanying drawings, same reference notation and terminology (i.e., numbers, letters, and/or symbols), refer to same system units, system sub-units, devices, assemblies, sub-assemblies, mechanisms, structures, components, elements, and configurations, and, peripheral equipment, utilities, accessories, and materials, components, elements, and/or parameters.

As a means of illustration, the system will be described for application during tobacco processing, but substantially the same system could be applied during the processing of other agricultural products.

The forms disclosed herein are generally focused on the domains encompassing the manufacturing or processing of tobacco, blend components or samples, and are specifically focused on the domains encompassing the automatic monitoring of tobacco processing, including aging or fermentation, etc., performed via hyperspectral imaging and analysis. However, it should be understood that the forms disclosed herein could be applied to other domains encompassing the manufacturing or processing of tea, fruits, during the production of fruit juices, grapes for the production of wines, as well as a vast array of other agricultural products.

As may be appreciated, the systems and methods described herein have multiple utilities. With regard to tobacco processing, in one form, tobacco samples may be monitored during a particular process, such as aging or fermentation, to assess their progress and adjust process parameters, either manually or automatically, to achieve an optimum result.

In hyperspectral imaging, a field of view of a sample is scanned and imaged while the sample is exposed to electromagnetic radiation. During the hyperspectral scanning and imaging there is generated and collected relatively large numbers of multiple spectral images, one-at-a-time, but, in an extremely fast sequential manner of the objects emitting electromagnetic radiation at a plurality of wavelengths and frequencies, where the wavelengths and frequencies are associated with different selected portions or bands of an entire hyperspectrum emitted by the objects. A hyperspectral imaging and analysis system can be operated in an extremely rapid manner for providing exceptionally highly resolved spectral and spatial data and information of an imaged sample of matter, with high accuracy and high precision, which are fundamentally unattainable by using standard spectral imaging and analysis.

In general, when electromagnetic radiation in the form of light, such as that used during hyperspectral imaging, is incident upon an object, the electromagnetic radiation is affected by one or more of the physical, chemical, and/or biological species or components making up the object, by any combination of electromagnetic radiation absorption, diffusion, reflection, diffraction, scattering, and/or transmission, mechanisms. Moreover, an object whose composition includes organic chemical species or components, ordinarily exhibits some degree of fluorescent and/or phosphorescent properties, when illuminated by some type of electromagnetic radiation or light, such as ultra-violet (UV), visible (VIS), or infrared (IR), types of light. The affected electromagnetic radiation, in the form of diffused, reflected, diffracted, scattered, and/or transmitted, electromagnetic radiation emitted by the object is directly and uniquely related to the physical, chemical, and/or biological properties of the object, in general, and of the chemical species or components making up the object, in particular, and therefore represents a unique spectral fingerprint or signature pattern type of identification and characterization of the object.

A typical spectral imaging system consists of an automated measurement system and corresponding analysis software. The automated measurement system includes optics, mechanics, electronics, and peripheral hardware and software, for irradiating, typically using an illuminating source, a scene or sample, followed by measuring and collecting light emitted, for example, by fluorescence, from objects in the scene or sample, and for applying calibration techniques best suited for extracting desired results from the measurements. Analysis software includes software and mathematical algorithms for analyzing, displaying, and presenting, useful results about the objects in the scene or sample in a meaningful way.

The hyperspectral image of a scene or a sample could be obtained from commercially available hyperspectral imaging cameras from Surface Optics Corporation of San Diego, Calif., among others, or custom built according to the user needs.

Hyperspectral imaging can be thought of as a combination of spectroscopy and imaging. In spectroscopy a spectra is collected at a single point. Spectra contain information about the chemical composition and material properties of a sample, and consist of a continuum of values that correspond to measurements at different wavelengths of light. In contrast, traditional cameras collect data of thousands of points. Each point or pixel contains one value (black and white image) or three values for a color image, corresponding to colors, red, green, and blue. Hyperspectral cameras combine the spectral resolution of spectroscopy and the spatial resolution of cameras. They create images with thousands of pixels that contain an array of values corresponding to light measurements at different wavelengths. Or, in other words, the data at each pixel is a spectrum. Together the pixels and the corresponding spectra create a multi-dimensional image cube. The amount of information contained in an image cube is immense, and provides a very detailed description of the underlying sample.

Each spectral image is a three dimensional data set of voxels (volume of pixels) in which two dimensions are spatial coordinates or position, (x, y), in an object and the third dimension is the wavelength, ($\lambda$), of the emitted light of the object, such that coordinates of each voxel in a spectral image may be represented as (x, y, $\lambda$). Any particular wavelength, ($\lambda$), of imaged light of the object is associated with a set of spectral images each featuring spectral fingerprints of the object in two dimensions, for example, along the x and y directions, whereby voxels having that value of wavelength constitute the pixels of a monochromatic image of the object at that wavelength. Each spectral image, featuring a range of wavelengths of imaged light of the object is analyzed to produce a two dimensional map of one or more physicochemical properties, for example, geometrical shape, form, or configuration, and dimensions, and/or chemical composition, of the object and/or of components of the object, in a scene or sample.

Spectral profiles treat image cubes as a collection of spectra and provide a detailed and comprehensive description of the image cube as a whole. They use a set of characteristic spectra and their relative occurrences within an image cube to summarize the material composition of the sample. The number of characteristic spectra extracted will depend upon the variability in the material, and normally range from a few to a few dozen. Spectral profiles are created by matching each spectra in an image cube to a characteristic spectra. The number of spectra matched to each characteristic spectra are counted and normalized to create the spectral profile of an image cube. Thus, spectral profiles can be thought of as a fingerprint derived from the hyperspectral image cube of the tobacco sample.

In hyperspectral imaging, multiple images of each object are generated from object emitted electromagnetic radiation having wavelengths and frequencies associated with different selected parts or bands of an entire spectrum emitted by the object. For example, hyperspectral images of an object are generated from object emitted electromagnetic radiation having wavelengths and frequencies associated with one or more of the following bands of an entire spectrum emitted by the object: the visible band, spanning the wavelength range of about 400-700 nanometers, the infra-red band, spanning the wavelength range of about 700-3000 nanometers, and the deep infra-red band, spanning the wavelength range of about 3-12 microns. If proper wavelengths and wavelength ranges are used during hyperspectral imaging, data and information of the hyperspectral images could be optimally used for detecting and analyzing by identifying, discriminating, classifying, and quantifying, the imaged objects and/or materials, for example, by analyzing different signature spectra present in pixels of the hyperspectral images.

A high speed hyperspectral imaging system is often required for different types of repeatable and non-repeatable chemical and physical processes taking place during the sub-100 millisecond time scale, which cannot, therefore, be studied using regular hyperspectral imaging techniques. Combustion reactions, impulse spectro-electrochemical experiments, and inelastic polymer deformations, are examples of such processes. Remote sensing of objects in distant scenes from rapidly moving platforms, for example, satellites and airplanes, is another example of a quickly changing observable that is often impossible to repeat, and therefore requires high speed hyperspectral imaging.

Disclosed herein, is a method, and system for monitoring the manufacturing of an agricultural product, such as tobacco, via hyperspectral imaging and analysis. In certain forms thereof, provided are methodologies, protocols, procedures and equipment that are highly accurate and highly precise, in that they are reproducible and robust, when evaluating agricultural products, such as tobacco. The testing methodologies disclosed herein exhibit high sensitivity, high resolution, and high speed during automatic on-line operation.

Certain forms disclosed herein are specifically focused on the domain encompassing measuring, analyzing, and determining, micro scale properties, characteristics, features, and parameters of agricultural products, such as tobacco, generally with respect to individual tobacco samples, and specifically with respect to single or individual tobacco leaves contained within the tobacco samples, and more specifically with respect to a wide variety of numerous possible physical, chemical, and/or biological properties, characteristics, features, and parameters of single or individual tobacco leaves contained within a given tobacco bale, lot or sample. In one form, provided is an automatic on-line process monitoring system employing hyperspectral imaging and analysis.

Certain forms disclosed herein use what will be referred to as "hyperspectrally detectable and classifiable codes." As used herein, a "hyperspectrally detectable and classifiable code" is a micro scale property, characteristic, feature, or parameter of a particular bulk agricultural product, such as a tobacco sample, which is hyperspectrally detectable by hyperspectral imaging and analysis in a manner that the resulting hyperspectral data and information, for example, hyperspectral "fingerprint" or "signature" patterns are usable for classifying at least part of a single or individual tobacco leaf contained within that particular tobacco sample. In turn, the classified part of the single or individual tobacco leaf contained within that particular tobacco sample is usable as part of a procedure for monitoring tobacco processing and may also be used to propose or make process adjustments to achieve desirable results.

Accordingly, a "hyperspectrally detectable and classifiable code" is defined, generally with respect to a particular individual agricultural product, such as a tobacco sample, and specifically with respect to a single or individual tobacco leaf contained within the particular tobacco sample, and more specifically with respect to a physical, chemical, and/or biological property, characteristic, feature, or parameter, of that single or individual tobacco leaf contained within that particular tobacco sample. The hyperspectrally detectable and classifiable codes are usable as part of a procedure for (uniquely and unambiguously) monitoring the processing or manufacturing of an agricultural product, such as tobacco.

Primary examples of micro scale testing for generating hyperspectrally detectable and classifiable codes, include: physical (geometrical/morphological) shape or form and size dimensions of single or individual tobacco leaves; coloring of single or individual tobacco leaves; moisture (water) content of, or within, single or individual tobacco leaves; type, distribution, and compositional make-up, of (organic and inorganic) chemical species or components, of single or individual tobacco leaves; types, distribution, and compositional make-up, of possible unknown or foreign (physical, chemical, and/or biological) matter or species and aspects thereof on, and/or within, single or individual tobacco leaves; activity and/or reactivity of single or individual tobacco leaves in response to physical stimuli or effects, such as exposure to electromagnetic radiation; activity and/or reactivity of single or individual tobacco leaves in response to chemical stimuli or effects, such as exposure to aqueous liquids or to non-aqueous (organic based) liquids; and activity and/or reactivity of single or individual tobacco leaves in response to biological stimuli or effects, such as exposure to biological organisms; physical (geometrical/morphological) shape or form and size dimensions of single or individual tobacco leaves; coloring of single or individual tobacco leaves; moisture content of, or within, single or individual tobacco leaves; types, distribution, and compositional make-up, of (organic and inorganic) chemical species or components, of single or individual tobacco leaves; types, distribution and compositional make-up of possible unknown or foreign (physical, chemical, and/or biological) matter or species and aspects thereof on, and/or within, single or individual tobacco leaves; activity and/or reactivity of single or individual tobacco leaves in response to physical stimuli or effects, such as exposure to electromagnetic radiation; activity and/or reactivity of single or individual tobacco leaves in response to chemical stimuli or effects (such as exposure to aqueous (water based) liquids or to non-aqueous (organic based) liquids); and activity and/or reactivity of single or individual tobacco leaves in response to biological stimuli or effects, such as exposure to biological organisms.

Accordingly, provided is a method for monitoring the manufacturing or processing of an agricultural product, the method utilizing hyperspectral imaging and comprising: scanning at least one region along a sample of agricultural product using at least one light source of a single or different wavelengths; generating hyperspectral images from the at least one region; determining a spectral fingerprint for the sample of agricultural product from the hyperspectral images; and comparing the spectral fingerprint so obtained to a spectral fingerprint database containing a plurality of fingerprints obtained at various points of the manufacturing process, using a computer processor, to determine which point in the manufacturing process the sample has progressed to.

The method is based upon obtaining hyperspectral signatures for the agricultural material being processed to minimize or eliminate the need for human evaluation during processing. To accomplish this, first a standard database is created that includes hyperspectral signatures taken at each step of a process, such as a tobacco aging or fermentation process. The database so obtained is used as a benchmark against which the process will be monitored at each step or stage of the process. Adjustments can them be made to the process on a real-time basis, by controlling the processing parameters to ensure the quality of the final product.

The method may comprise scanning multiple regions along the sample of agricultural product using at least one light source of a single or different wavelengths; and generating hyperspectral images from the multiple regions. The method may further comprise determining a code for the sample.

The agricultural product may comprise tobacco. The tobacco may be in the form of a sample. At least one light source may be positioned to minimize the angle of incidence of each beam of light with the bale of tobacco. Cost of the samples being processed may be a factor used by the computer processor in monitoring and process adjustment.

The method may further comprise repeating the steps of scanning at least one region along a sample of agricultural product using at least one light source of different wavelengths, generating hyperspectral images from the at least one region, and forming a spectral fingerprint for the sample of agricultural product from the hyperspectral images, for a plurality of samples of agricultural product during the processing of the agricultural product.

The method may further comprise storing spectral fingerprints data from a plurality of samples of agricultural product taken at various stages of processing within computer storage means to form a process database.

Further provided is a system monitoring the manufacturing or processing of an agricultural product, according to the methods described above.

Also provided is a method for determining the stage of processing for an agricultural product. The method utilizes hyperspectral imaging and includes the steps of scanning multiple regions along a sample of a desirable agricultural product using at least one light source of different wavelengths; generating hyperspectral images from the multiple regions; forming a spectral fingerprint for the sample from the hyperspectral images; and correlating the spectral fingerprint so obtained to a spectral fingerprint database containing a plurality of fingerprints obtained at various points of processing, using a computer processor, to determine the stage of processing.

The method may further comprise storing data about the spectral fingerprint within a computer storage means, and repeating the steps of scanning multiple regions along a sample of a desirable agricultural product using at least one light source of a single or different wavelengths, generating hyperspectral images from the multiple regions, forming a spectral fingerprint for the sample from the hyperspectral images, storing data about the spectral fingerprint within a computer storage means, using a plurality of desirable agricultural products. The desirable agricultural product may be an unprocessed, semi-processed or fully processed agricultural product, such as tobacco.

Figure 2:
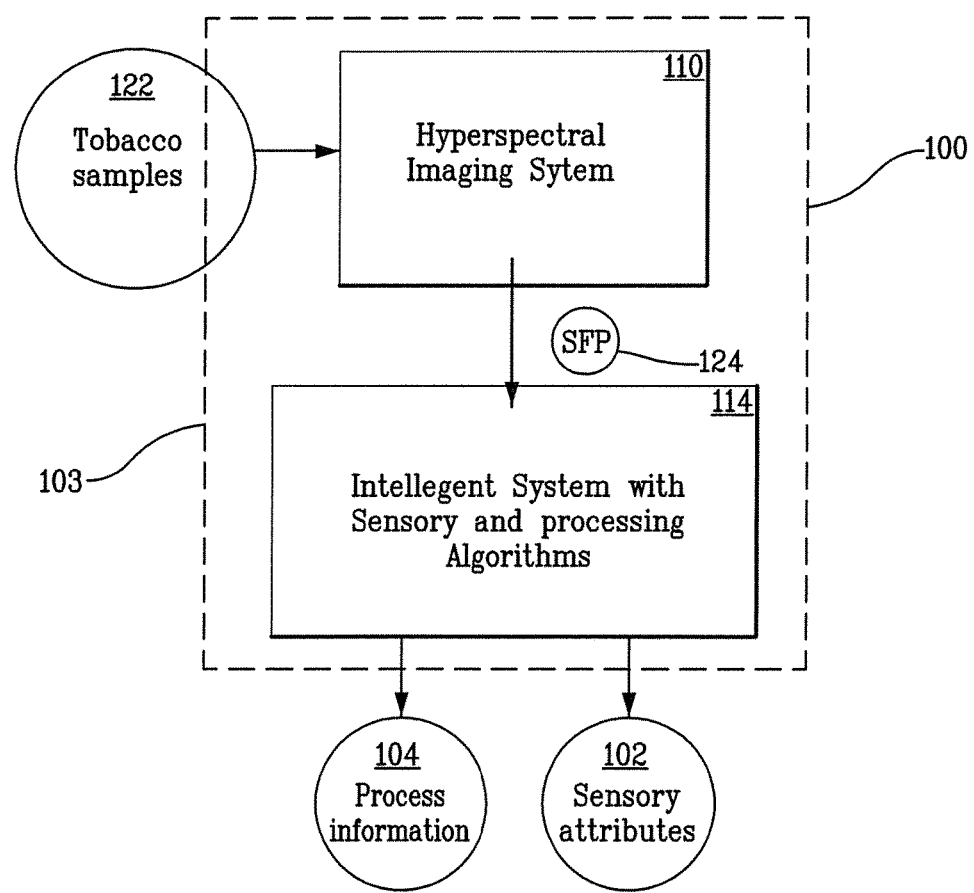
FIG. 2 presents, in block diagram form, a second stage of a system for monitoring the manufacturing of an agricultural product, in accordance herewith.

While the invention is described in detail for the case of processing tobacco, it should be understood that tobacco is used only to illustrate the methods and systems contemplated herein and not so as to limit the application of the methods and systems described herein. Referring to FIGS. 1 and 2, disclosed herein is a method and system, for monitoring the manufacturing or processing of an agricultural product 100 to determine the sensory attributes 102, which can be used to assess the stage of processing utilizing process information 104. The system 100 uses spectral fingerprints 106 and 124 obtained by hyperspectral imaging system 110. Each spectral fingerprint 106 or 124 gives a measure of the physical and chemical characteristics of the tobacco sample 108 or 122 (or other agricultural raw material). The physical and chemical characteristics determine the sensory attributes and stage of processing of the different tobacco samples 108 or 122. By building a database of the spectral fingerprints 106 of various tobacco at different stages of processing, an intelligent system 118 can be built based upon statistical prediction and/or neural network and artificial intelligence techniques 120 to develop a system for monitoring the manufacturing or processing of an agricultural product 100. The algorithm can be optimized for cost reduction by including the cost of different tobacco samples together with the cost to process them, as one of the variables used in an optimization scheme.

Referring to FIG. 1, in a first stage 101 of the system 100, a database is built with existing tobacco samples 108 taken at different stages of processing and the hyperspectral fingerprints 106 and the subjective sensory attributes 116 of tobacco samples. An intelligent system 118 is built based upon a neural network or an artificial intelligence algorithm 120 that provides a mapping of the hyperspectral signature with the stage of processing and the subjective sensory attributes 116 obtained from a sensory panel 120. The costs of individual tobacco and its processing costs can also be used as independent parameters in the algorithm to optimize the processing scheme for sensory attributes and cost effectiveness. At the end of the first stage 101, there is formed a composite hyperspectral signature, which can be correlated to satisfactory sensory attributes.

Referring to FIG. 2, in a second phase 103, spectral fingerprints 124 of tobacco samples 122 are obtained at different levels of processing. The cost of each of these tobacco samples 122, both initial and cost to process to a certain level are also obtained and used as an input to the system 100. Intelligent system 114 will determine, using the expert system 118 developed in the first phase 101, whether additional processing is required, and whether process parameters require adjustment to obtain optimal cost and acceptable sensory attributes using the input parameters, the spectral fingerprints 124, and the cost information obtained for the samples.

Accordingly, provided is a method for monitoring a manufacturing process of an agricultural product. The method utilizes hyperspectral imaging and includes the steps of scanning at least one region along a sample of agricultural product using at least one light source of a single or different wavelengths; generating hyperspectral images from the at least one region; determining a spectral fingerprint for the sample of agricultural product from the hyperspectral images; and comparing the spectral fingerprint obtained in step (c) to a spectral fingerprint database containing a plurality of fingerprints obtained at various points of the manufacturing process, using a computer processor, to determine which point in the manufacturing process the sample has progressed to. In some forms, one or more features of a spectral fingerprint may be determined that correspond to the desirable sensory attributes. In some forms, one or more features of the spectral fingerprint of the sample of the agricultural product are correlated to the desirable sensory attributes.

The method may comprise scanning multiple regions along the sample of agricultural product using at least one light source of a single or different wavelengths; and generating hyperspectral images from the multiple regions. The method may further comprise determining a code for the sample.

The agricultural product may comprise tobacco. The tobacco may be in the form of a bale, lot or sample. At least one light source may be positioned to minimize the angle of incidence of each beam of light with the sample being imaged.

In some forms, cost of the samples and/or its processing may be a factor used by the computer processor.

In some forms, the agricultural product is tobacco and the manufacturing process is a fermentation process. In some forms, the method determines the time required to complete the fermentation process for the tobacco sample.

In some forms, the agricultural product is tobacco and the manufacturing process is a tobacco aging process. In some forms, the method determines the time required to complete the tobacco aging process for the tobacco sample.

As may be appreciated, the method disclosed herein may be computer implemented. In some forms, data about the spectral fingerprints of the plurality of samples of agricultural product are stored within a computer storage means.

Also provided is a method for determining the stage of processing for an agricultural product utilizing hyperspectral imaging. The method includes the steps of scanning multiple regions along a sample of a desirable agricultural product using at least one light source of different wavelengths; generating hyperspectral images from the multiple regions; forming a spectral fingerprint for the sample from the hyperspectral images; and correlating the spectral fingerprint obtained in step (c) to a spectral fingerprint database containing a plurality of fingerprints obtained at various points of processing, using a computer processor, to determine the stage of processing.

In another aspect, provided is a method of determining the stage of processing for a product. The method includes the steps of resolving whether a sample meets a desired attribute for the product and if so, applying hyperspectral imaging analysis and theoretic analysis to establish a relationship P comprising unique spectra of the sample, said unique spectra comprising at least two spectral elements x and y and values thereof; establishing through hyperspectral imaging analysis a characterization of the sample according to said spectral elements (at least x and y) of said unique spectra P; and mathematically resolving from said characterizations to determine whether the sample achieves the values of said spectral elements of P.

Figure 3:
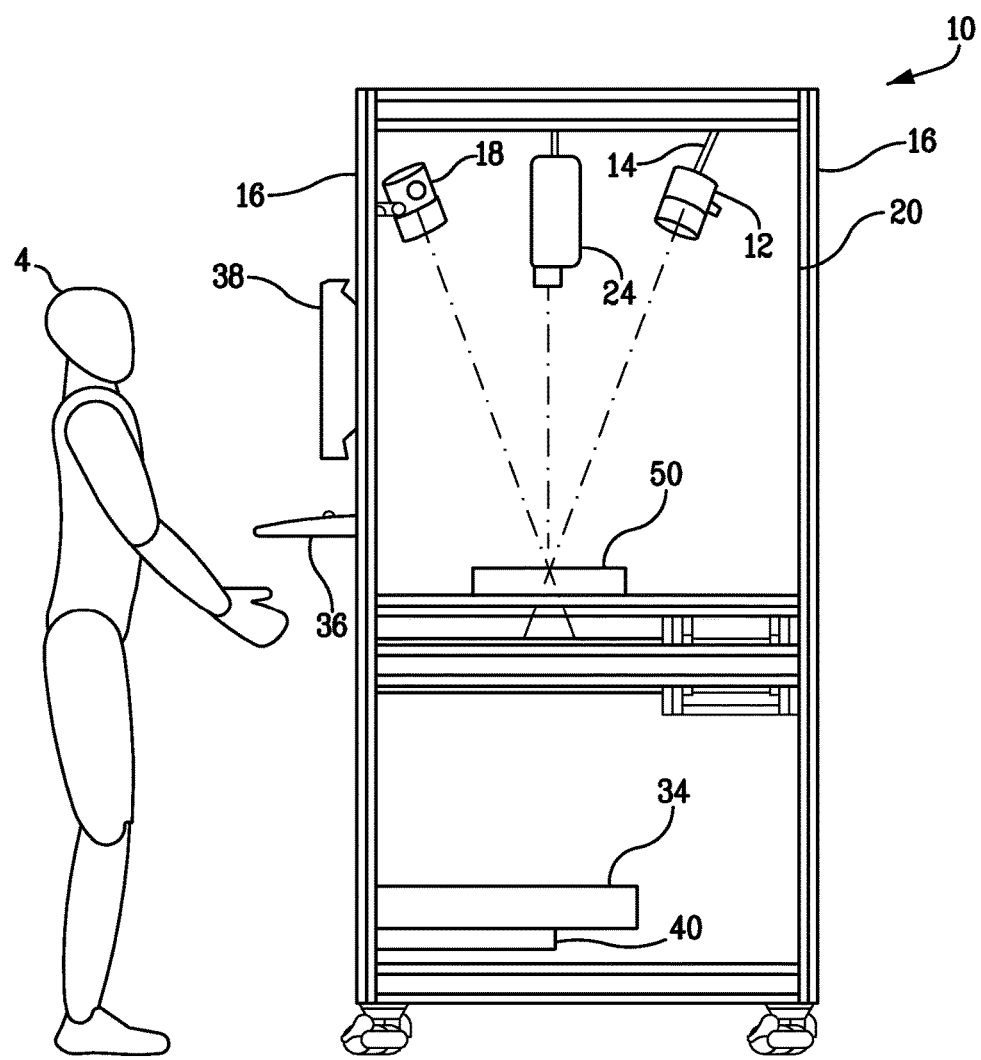
FIG. 3 presents an example of an implementation of a system for scanning an agricultural product employing hyperspectral imaging and analysis, in accordance herewith.

Referring now to FIG. 3, a system 10 for monitoring a manufacturing process of an agricultural product P employing hyperspectral imaging and analysis is shown in schematic form. The system 10 includes at least one light source 12 for providing a beam of light. As shown, the at least one light source 12 may be mounted on an arm 14 for positioning at least one light source 12 in proximity to the agricultural product (not shown), which may be positioned on platform 50. In one form, arm 14 is mounted to frame 16 of cabinet 20 and may be either fixed thereto or moveably positionable, as will be described hereinbelow. As shown in FIG. 3, a second light source 18 may also be provided and mounted to frame 16 of cabinet 20 or, optionally, to an arm (not shown), which in turn is mounted to frame 16 of cabinet 20.

In one form, the at least one light source 12 for providing a beam of light of different wavelengths comprises a tungsten, halogen or a xenon light source. In another form, the at least one light source 12 for providing a beam of light comprises a mercury light source. In yet another form, the at least one light source or the second light source 18 comprises an ultraviolet light source for use in providing a chemical signature of the agricultural product P. This optional ultraviolet light source adds an additional media of classification that provides a better understanding of an agricultural product's characteristics. In still yet another form, the at least one light source 12 comprises a xenon light source, the second light source 18 comprises a mercury light source and a third light source (not shown) comprises an ultraviolet light source.

In one form, the at least one light source 12 and/or the second light source 18 may be positioned to minimize the angle of incidence of a beam of light with the agricultural product P.

In order to segregate ambient light from the light provided by system 10, walls (not shown) may be added to cabinet 20 to form an enclosure to provide a dark-room-like environment for system 10.

The hyperspectral image of a scene or a sample is obtained using hyperspectral imaging camera 24.

Referring still to FIG. 3, a computer 40 having a processor capable of rapidly handling system data is provided and programmed to compare the detected component wavelengths to a database of previously analyzed agricultural products to identify agricultural product P. Computer 40 may be a personal computer having an Intel® Core™2 Quad or other processor. Computer 40 may also control the operation of the system 10 and the positioning of the head unit 20 about agricultural product P. A device 34 for providing an uninterrupted source of power to computer 40 may be provided, such devices readily available from a variety of commercial sources. As is conventional, computer 40 may also include a keyboard 36 and monitor 38 to enable input and system monitoring by a user U. A regulated power supply 34 may be provided to assure that a tightly controlled source of power is supplied to system 10.

Test results are based on the scanning and counting of individual samples, each comprising dozens of scans, and each sample classified using spectral band features, spectral finger prints (SFP), major spectral representative components, purity and quality of each major compound (component, SFP), relative quantity of each SFP and, optionally, crystallization and morphological features.

A plurality of samples of agricultural products, such as tobacco samples at various stages of processing is scanned. As indicated, for agricultural products such as tobacco, a significant number of samples should be scanned in order that the impact of sample variability is reduced. In practice, it has been observed that the impact due to this variability can be reduced when the number of samples N is about 5 to about 25. However, by carefully selecting representative samples, fewer samples could be used to incorporate all the normal variations observed in processing a particular product. Applying this technique to tobacco, tobacco samples may be scanned using xenon and/or mercury and/or tungsten, and/or halogen light sources and an optional ultraviolet light source may be used for chemical signature classification.

In operation, the light source(s) is activated (one, two, three or more spot lights in parallel to the region of interest (ROI)), permitting redundant data to be gathered. A plurality of regions of interest (such as by way of example, but not of limitation, a 20 cm×20 cm area for each ROI) is scanned for each sample to provide one, two, three or more hyperspectral images. Scanning is performed and the reflection spectral signature and optional fluorescence spectral chemical signature received. The images are then saved and a database (including labels identifying the particular sample and/or lot) is thus formed from the combined information obtained for the N samples During scanning, the hyperspectral camera system provides a three dimensional hyperspectral image cube. The image cube, which may be, by way of example, but not of limitation, on the order of about a 696 pixel by 520 pixel array. Such a picture or frame would thus contain 361,920 pixels. As may be appreciated by those skilled in the art, each pixel may contain about 128, 256, 500 or more spectra points at different wavelengths for an agricultural product such as tobacco.

Figure 4:
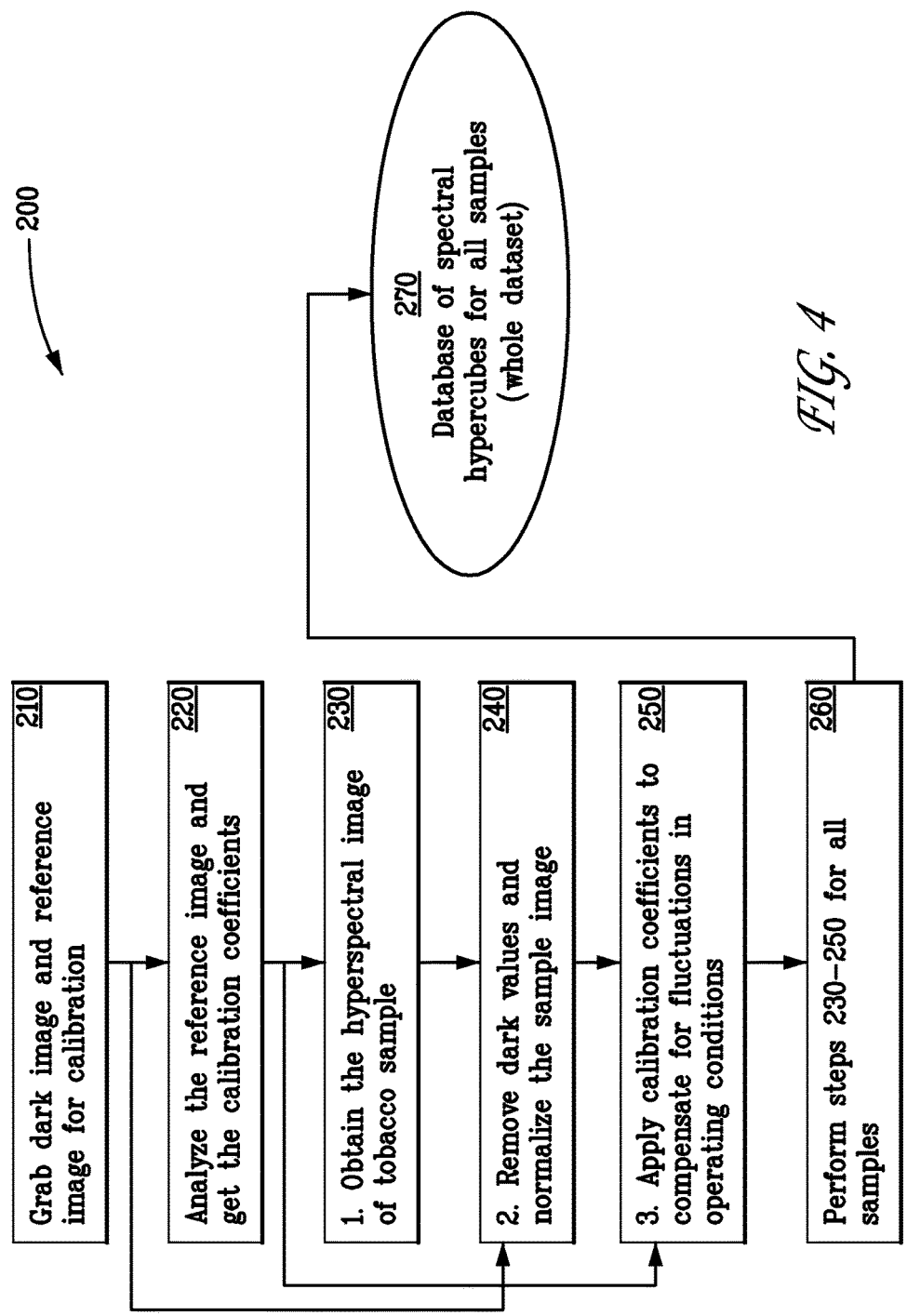
FIG. 4 presents a method for analyzing data to create a spectral library, in accordance herewith.

Referring now to FIG. 4, an algorithm 200 for use in the system and methods described herein will now be disclosed. In step 210, a dark image and reference image are obtained for use in system calibration. In step 220, the reference image is analyzed and calibration coefficients are obtained. In step 230, a hyperspectral image of a tobacco sample is obtained. In step 240, using the information obtained during calibration, dark values are removed and the sample image normalized. In step 250, calibration coefficients are applied to compensate for fluctuations in operating conditions (e.g., light intensity, ambient conditions, etc.). In step 260, steps 230-250 are repeated for all samples and the data so obtained is added in step 270 to the database of spectral hypercubes (whole dataset). It should be understood that the algorithm for creating the database as illustrated in FIG. 4 is referenced to tobacco samples by way of illustration only and not as limiting. The same steps could be used to create the whole spectral database for application in other agricultural products like tea, fruits grapes or other products. The result is 350, a spectral library for all the samples that could be used to assess and monitor processing of the agricultural product, which contains the spectral fingerprints of the dataset found in step 340, and the unique spectra found in step 330.

Figure 5:
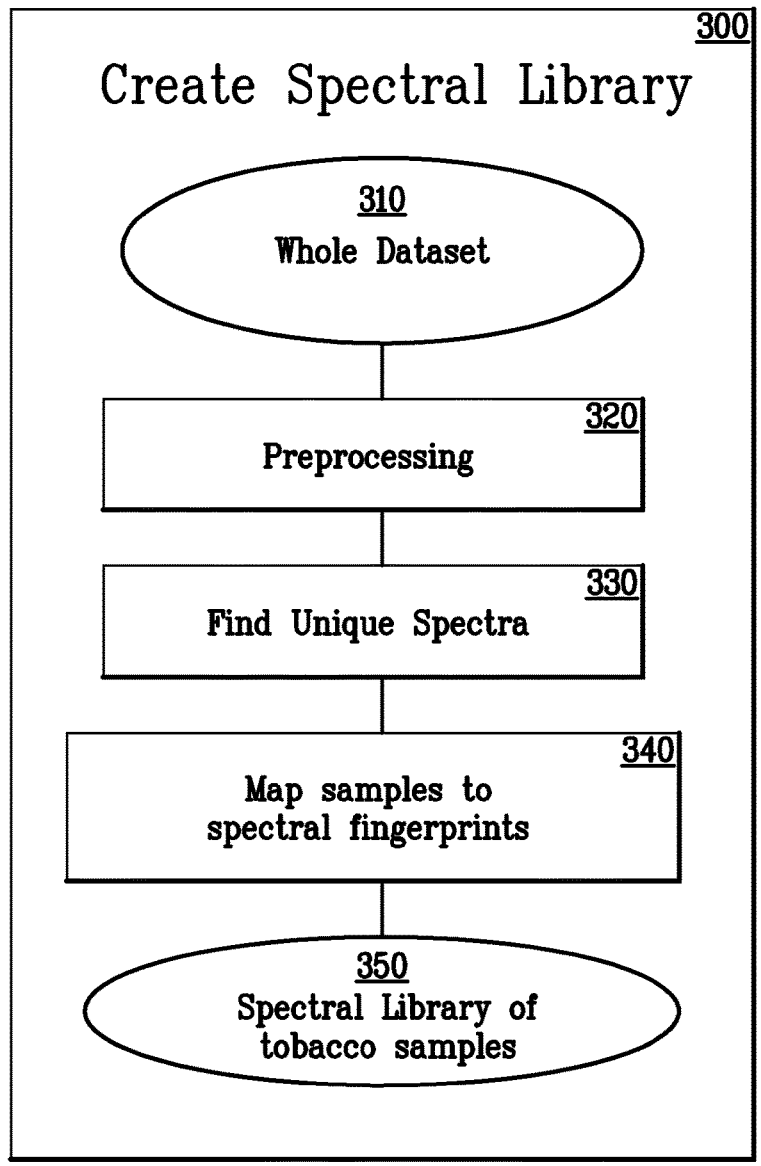
FIG. 5 presents a method for analyzing data to create a spectral library, in accordance herewith.

Referring now to FIG. 5, a method for analyzing data to create a spectral library of samples 300, in accordance herewith is shown. Spectral library 300 is formed by obtaining a dataset in step 310. In step 320, the dataset is preprocessed. Unique spectra, indicative of the dataset, are identified in step 330. In step 340, spectral distributions (spectral fingerprints) are found for each of the samples using the unique spectra found in step 330.

In some forms, following imaging, several data processing routines are performed to reduce noise, increase consistency, enhance spectra for feature extraction, and reduce computation time. The data processing routines are summarized below.

Spectral binning is used to produce more consistent signals, reduce file size, and decrease processing time. Spectral binning is an operation performed on each spectra of the image cube, and consists of summation of adjacent wavelengths to produce a down-sampled spectra. Down-sampled spectra have less resolution, but increased signal to noise ratio. A sampling rate was chosen that creates a signal with maximum compression and minimal loss of fidelity. This is followed by median filtering to reduce the noise and increase the signal to noise ratio.

Spatial Binning is applied to the image cube, and consists of down-sampling via summation of adjacent pixels. Pixels contain spectra, so spatial binning results in summation of adjacent spectra. This increases signal to noise ratio, reduces file size, and decreases processing time. Information loss is minimal because the camera is selected to provide a high resolution. Summation allows for each pixel's spectra to contribute to the down-sampled spectra, and adjacent pixels are usually from the same part of the leaf, which tend to have similar spectra. Similar effects may be achieved by using a Gaussian filter to increase spatial coherency and to reduce "salt and pepper" pixel classification. A Gaussian filter may be useful when spatial reduction is not desirable.

In some forms, image correction may be performed by first collecting dark images twice daily. These are then used during processing to estimate and remove sensor noise. The dark image processing procedure consists of two steps. Dark images' spectra, $d_j \epsilon D_i$ are first binned to be consistent with other images cubes. Then the spectral mean, $d^{mean;i}$ is calculated (Eq. 1) and used to estimate sensor noise.

$$\vec{s}_i^{mean} = \left\| \sum^{\forall \vec{s}_j \in S_1} \vec{s}_j \right\| \quad (1)$$

During data processing $d^{mean;}i$ is removed from each spectra of each sample by subtraction. This is a standard method of removing sensor noise.

Reference image cubes, $R_i$ are collected twice-daily and contain spectra that can be used to measure and correct lighting inconsistencies. Applying a correction based on the reference image will also eliminate any sensor drift or variation over time. This step is very important as any changes in either the lighting conditions or the sensor response drift will adversely affect the system performance. Also, pixels of shadow have low signal to noise ratio and should be eliminated.

Most signals tend to have a maximum peak created by the spectral signature of the light whose value is proportional to the amount of light hitting the sensor, and the sensor's response. For this reason shadow detection is applied using maximum peak thresholding.

$$pixel = \begin{cases} \text{not shadow} & : \max(\vec{s}_i) \geq \text{thresh} \\ \text{shadow} & : \max(\vec{s}_i) < \text{thresh} \end{cases}$$

where max(si) returns the maximum component of the spectra, si.

Spectra with a max peak less than a user-defined threshold are tagged as shadow spectra, and ignored during spatial binning, spectral binning, local spectra extraction, and spectra matching.

Image cubes of tobacco samples contain thousands of spectra, many of which are nearly identical and correspond to similar material properties and sensorial effects. The information contained in the image cube can be summarized as a spectral profile using a set of characteristic spectra and their occurrence rate within a sample. Construction of a spectral profile consists of two primary steps.
1. Spectra Extraction—finding characteristic spectra.
2. Spectra Matching—matching an image cube's spectra to characteristic spectra.

The first step of building a spectral profile is to create a set of characteristic spectra often called end-members. End-members are often manually selected by choosing pixels that are known to correspond to a specific class or contain a unique material. For many agricultural products, including tobacco, distinct characteristics can be very difficult to detect manually and class specific spectra are non-existent. In such cases an automated spectra extraction technique is preferable.

Spectra extraction differs from other automated end-member extraction techniques in that it divides the spectral feature space using an evenly spaced grid. Spectra extraction finds all spectra in a data set that are more dissimilar than a user-defined threshold, $\alpha^*$. The assumption is that if two spectra are more similar than $\alpha^*$ they represent identical materials and can be considered duplicates. By finding all dissimilar spectra in a data set, all unique materials can be found. Other automated spectra extraction algorithms are often associated with un-mixing models, which assume individual pixels contain a combination of unique spectral signatures from multiple materials. Sequential Maximum Angle Convex Cone (SMACC) and Support Vector Machine-Based End-member extraction are two examples. The technique disclosed herein was chosen for simplicity. Un-mixing models may not be appropriate for smaller scale agricultural imaging, where individual pixel size is in millimeters as opposed to aerial imaging, where individual pixel size is usually in meters. The spectra extraction procedure disclosed herein first analyzes image cubes independently in a step called local spectra extraction. The results are then combined during global spectra extraction. Extraction in this order decreases processing time and allows for outliers of individual image cubes to be eliminated.

Once the characteristic spectra of the data set have been extracted, spectra matching step is applied on each image cube. Each $s_j \epsilon S_i$ is matched with the most similar $c_k \epsilon C_{all}$. As an image cube is analyzed, a tally of the number of matches for each $c_k \epsilon C_{all}$ is kept as a spectral profile, $p_i$. Each component of $p_i$ corresponds to the number of matches for a single $c_k \epsilon C_{all}$. Once all $s_j \epsilon S_i$ have been matched $p_i$ is normalized and represents the percent occurrence rate of each $c_k \epsilon C_{all}$ in Si.

The inclusion of unidentified pixels can be advantageous for certain scenarios such as when tobacco samples are contaminated with non-tobacco material, if shadow detection is unreliable, or if only a selected few spectra should be included in the spectral profiles. Rather than forcing a match with the most similar $c_k \epsilon C_{all}$, Spectra that are more dissimilar than $\alpha^{}$ to all $c_k \epsilon C_{all}$ are counted as unidentified. Unidentified pixels do not contribute to the spectral profile. $\alpha^{}$ is a user-defined parameter, and larger values of $\alpha^{**}$ will allow more dissimilar spectra to match to $c_k \epsilon C_{all}$, while small values will allow matches with only similar spectra. Setting a high $\alpha^*$ will force a match with the closest $c_k \epsilon C_{all}$.

Since previous hyperspectral image classification problems have focused on pixel by pixel classification, spectra matching is often the goal of hyperspectral image analysis. These applications often make use of machine learning algorithms such as support vector machines and decision trees to classify spectra. Matching in this manner requires a training set of characteristic spectra which is not practical. Fully automated techniques are preferable, and also may use spectral feature fitting (SFF). SFF is designed to distinguish between spectra using specific features of a spectra. While SFF can achieve successful results, SAM is a more appropriate measure, since it is intended to find the similarity between two spectra using all the bands as confirmed by the results.

The goal of feature selection is to choose a subset of features capable of summarizing the data with little or no information loss. It is applied before classification to avoid dimensionality, which often reduces classification performance. Spectral profiles can contain redundant features, particularly when the spectra extraction threshold, $\alpha^*$ is low. Experimental work suggests that selection of an appropriate $\alpha^*$ combined with the ability of support vector machines (SVM) to handle redundant and/or uninformative features eliminates the need for a feature selection step. However in some cases we found that choosing the optimal subset of features using the Jeffreys-Matusita Distance as an information measure was effective.

In some forms, classification may be conducted using well-known procedures, by way of example and not of limitation, discriminant analysis, SVM, neural networks, etc., as those skilled in the art will recognize.

As may be appreciated, the amount of raw data is very large, due to the large number of pixels existing within a particular image cube. A separate spectral is obtained for each pixel. Advantageously, the method disclosed herein identifies a set of characteristic spectra for the whole dataset. The composition of the spectra provides a signature for the sample, with similar samples having similar signatures or fingerprints. Unique spectral fingerprints are then identified for each tobacco sample and for each stage of processing.

The spectral library or database of the samples developed in FIG. 5 may be used to gauge the progression of a manufacturing process, such as tobacco ageing or fermentation. This information may also be used in a closed system capable of making adjustments to process parameters, such as temperature, air flow, humidity, etc. to optimize desirable sensory attributes.

Advantageously, the method and system disclosed herein provides a chemical imaging platform that enables speed and exceptionally high sensitivity, thus accurate and non-destructive nature, wherein measurement time is greatly reduced. This enables the tracking of the monitored material with high repeatability.

The method and system disclosed herein provides a highly sensitive hyper spectral imaging analyzer with co-sharing database capabilities. The digitized highly sensitive imaging system disclosed herein enables the imaging of materials components, more detailed observation and provides more specific, sensitive, accurate and repeatable measurements. This may be achieved using advanced image recognition technologies, as well as adaptive and collaborative data bases and statistical and optimization algorithms.

The method and system disclosed herein is capable of characterizing the composition of inorganic, organic, and chemical particulate matter suspended in agricultural products such as tobacco. The instrument scans leaf or other samples, analyses the scanned samples' wavelength signature, performing trends analysis and compares the gathered data to data bases that may, in one form, be continuously updated. The system then generates reports for system users. A remote network may be provided to support the gathering of data for integrated database construction as well as to support remote professional personnel in real time.

Advantageously, the proposed method requires no sample preparation. In operation, linear calibration plots in the ppm range are obtained for mono-component contamination and for simple compound mixtures in this matrix. Non-contact, non-destructive, near real time on-line, automated physico-chemical imaging, classification and analysis of a sample of tobacco leaves or other agricultural products is provided without the need for consumable materials for sample processing. The system operates using algorithms and software packages, together with unique ultra-high resolution optical components and a two-dimensional sample positioning of regions of interest for generating, for example, five dimensional (5D) spectral images of the tobacco sample under analysis.

All or a portion of the devices and subsystems of the exemplary forms can be conveniently implemented using one or more general purpose computer systems, microprocessors, digital signal processors, microcontrollers, and the like, programmed according to the teachings of the exemplary forms disclosed herein, as will be appreciated by those skilled in the computer and software arts.

In view thereof, in one form there is provided a computer program product for monitoring a manufacturing process of an agricultural product, the computer program structured and arranged to determine one or more features of a spectral fingerprint that correspond to desirable sensory attributes, and/or determining processing parameters, including one or more computer readable instructions embedded on a tangible computer readable medium and configured to cause one or more computer processors to perform the steps described above and transmitting information relating to the steps described above over a communications link.

Appropriate software can be readily prepared by programmers of ordinary skill based on the teachings of the exemplary forms, as will be appreciated by those skilled in the software art. Further, the devices and subsystems of the exemplary forms can be implemented on the World Wide Web. In addition, the devices and subsystems of the exemplary forms can be implemented by the preparation of application-specific integrated circuits or by interconnecting an appropriate network of conventional component circuits, as will be appreciated by those skilled in the electrical art(s). Thus, the exemplary forms are not limited to any specific combination of hardware circuitry and/or software.

Stored on any one or on a combination of computer readable media, the exemplary forms disclosed herein can include software for controlling the devices and subsystems of the exemplary forms, for driving the devices and subsystems of the exemplary forms, for enabling the devices and subsystems of the exemplary forms to interact with a human user, and the like. Such software can include, but is not limited to, device drivers, firmware, operating systems, development tools, applications software, and the like. Such computer readable media further can include the computer program product of a form disclosed herein for performing all or a portion (if processing is distributed) of the processing performed in implementing the methods disclosed herein. Computer code devices of the exemplary forms disclosed herein can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the exemplary forms disclosed herein can be distributed for better performance, reliability, cost, and the like.

As stated above, the devices and subsystems of the exemplary forms can include computer readable medium or memories for holding instructions programmed according to the forms disclosed herein and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

The forms disclosed herein, as illustratively described and exemplified hereinabove, have several beneficial and advantageous aspects, characteristics, and features. The forms disclosed herein successfully address and overcome shortcomings and limitations, and widen the scope, of currently known teachings with respect to the processing of agricultural products such as tobacco.

The forms disclosed herein, provide for processing methodologies (protocols, procedures, equipment) for, by way of example, but not of limitation, tobacco samples, which are highly accurate and highly precise (reproducible, robust). The forms disclosed herein, provide high sensitivity, high resolution, and high speed (fast, at short time scales), during automatic operation, in an optimum and highly efficient (cost effective) commercially applicable manner.

As may be appreciated, the performance of the methods and systems disclosed herein is dependent of the number of regions and samples scanned, image sizes, light sources, filters, light source energy stability, etc.

EXAMPLES

Example 1

The operation of the system and a method of forming a database will now be described by way of this prophetic example.

The system is initiated and the light sources brought up to operating temperature. A dark image and reference image are obtained for system calibration. The reference image is analyzed and calibration coefficients are obtained. A hyperspectral image of a tobacco or other agricultural sample is obtained.

Using the information obtained during the aforementioned calibration, dark values are removed and the sample image normalized. Calibration coefficients are applied to compensate for fluctuations in operating conditions (e.g., light intensity, ambient conditions, etc.). Hyperspectral images for additional tobacco samples are obtained for additional samples of interest and all data so obtained is added to the database of spectral hypercubes (whole dataset).

A spectral library is formed from the database of spectral hypercubes by first preprocessing the data. Unique spectra, indicative of the dataset are identified and samples mapped to the spectral fingerprints so obtained. The unique spectra are then added to a spectral database of processing parameters and information.

Example 2

When a new batch of agricultural product is to be processed, first, a spectral distribution is obtained for this product based on the teachings of this invention.

A system of the type shown in FIG. 3 was used. The samples employed were taken at 1) a point prior to processing, at 2) an intermediate stage of processing and at 3) the end of processing. As described herein, a selection algorithm is used, the results of which provide the processing parameters necessary to obtain optimized processing.

Figure 6:
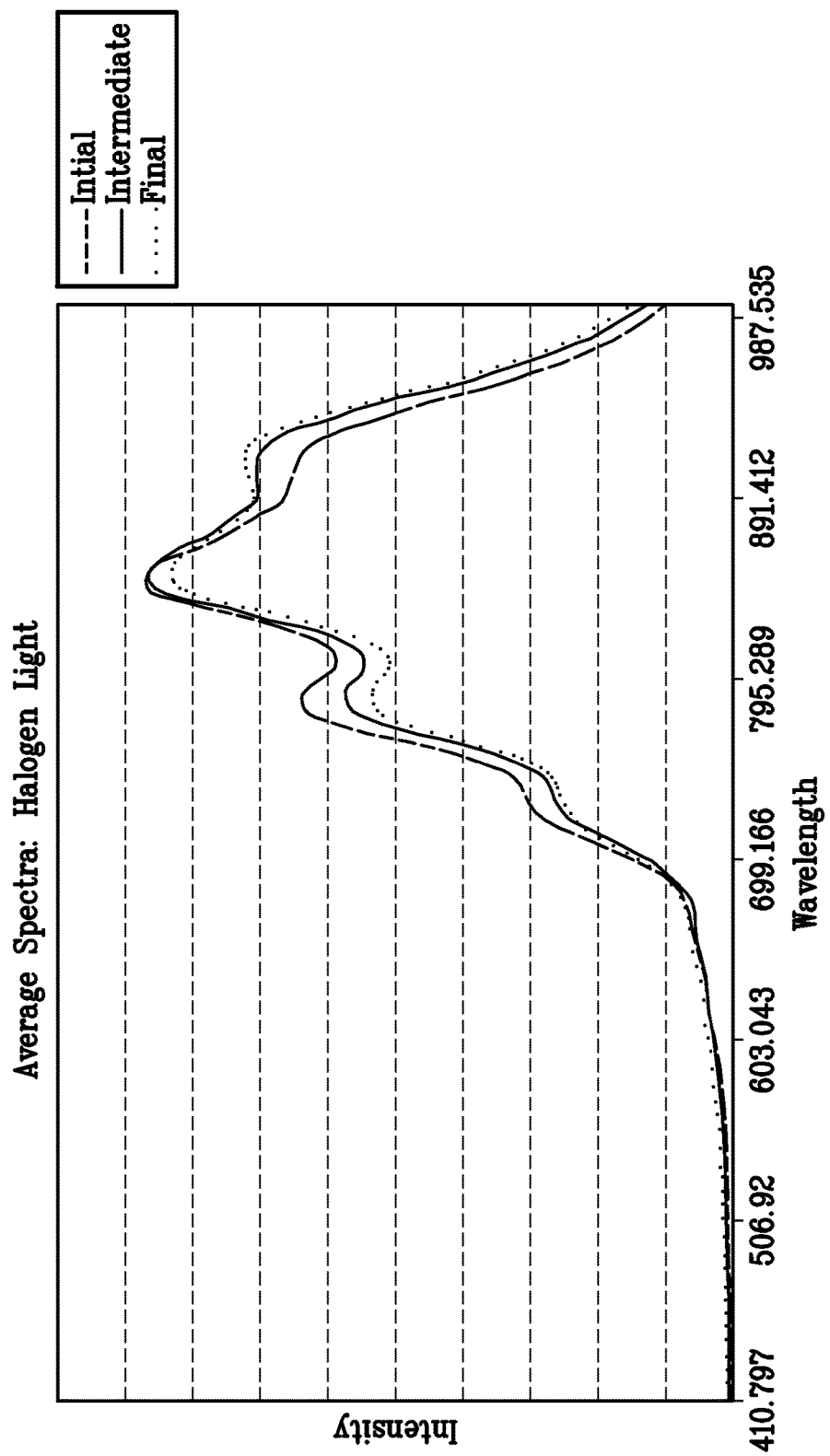
FIG. 6 presents a plot of intensity versus average spectra wavelength for tobacco samples at three stages of processing for a hyperspectral imaging and analysis system using halogen light, in accordance herewith.

Referring now to FIG. 6, a plot of intensity versus average spectra wavelength for tobacco samples at the three different stages of processing is presented for a hyperspectral imaging and analysis system using halogen light. As may be seen, excellent resolution was achieved, with each stage of processing discernible from the others.

Example 3

Once again, a system of the type shown in FIG. 3 was used. The samples employed were taken at 1) a point prior to processing, at 2) an intermediate stage of processing and at 3) the end of processing. As described herein, a selection algorithm is used, the results of which provide the processing parameters necessary to obtain optimized processing.

Figure 7:
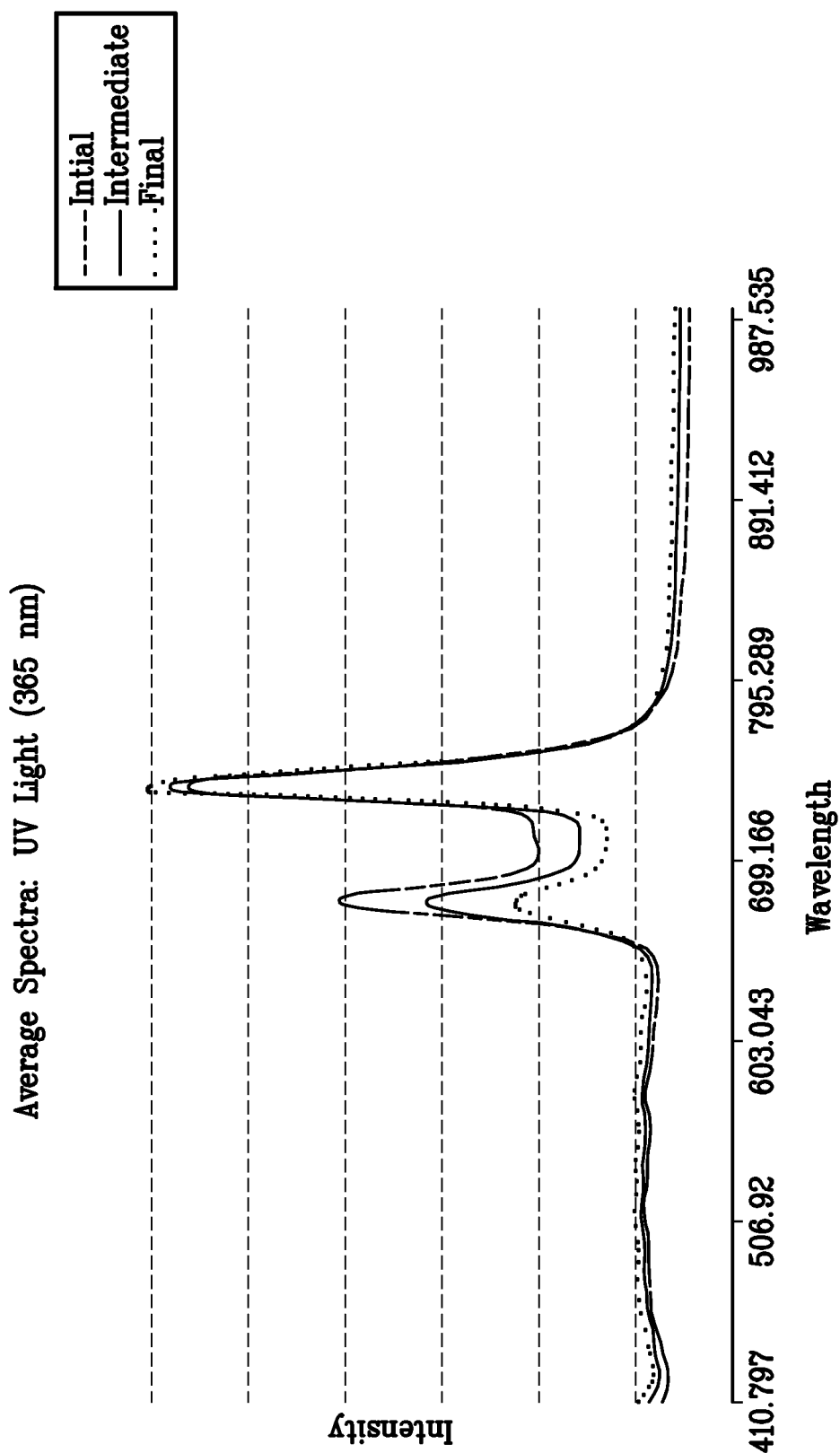
FIG. 7 presents a plot of intensity versus average spectra wavelength for tobacco samples at three stages of processing for a hyperspectral imaging and analysis system using UV light, in accordance herewith.

Referring now to FIG. 7, a plot of intensity versus average spectra wavelength for tobacco samples at the three different stages of processing is presented for a hyperspectral imaging and analysis system using UV light. As may be seen, excellent resolution was achieved, with each stage of processing discernible from the others.

Example 4

Once again, a system of the type shown in FIG. 3 was used. The samples employed were taken at 1) a point prior to processing, at 2) an intermediate stage of processing and at 3) the end of processing. As described herein, a selection algorithm is used, the results of which provide the processing parameters necessary to obtain optimized processing.

Figure 8:
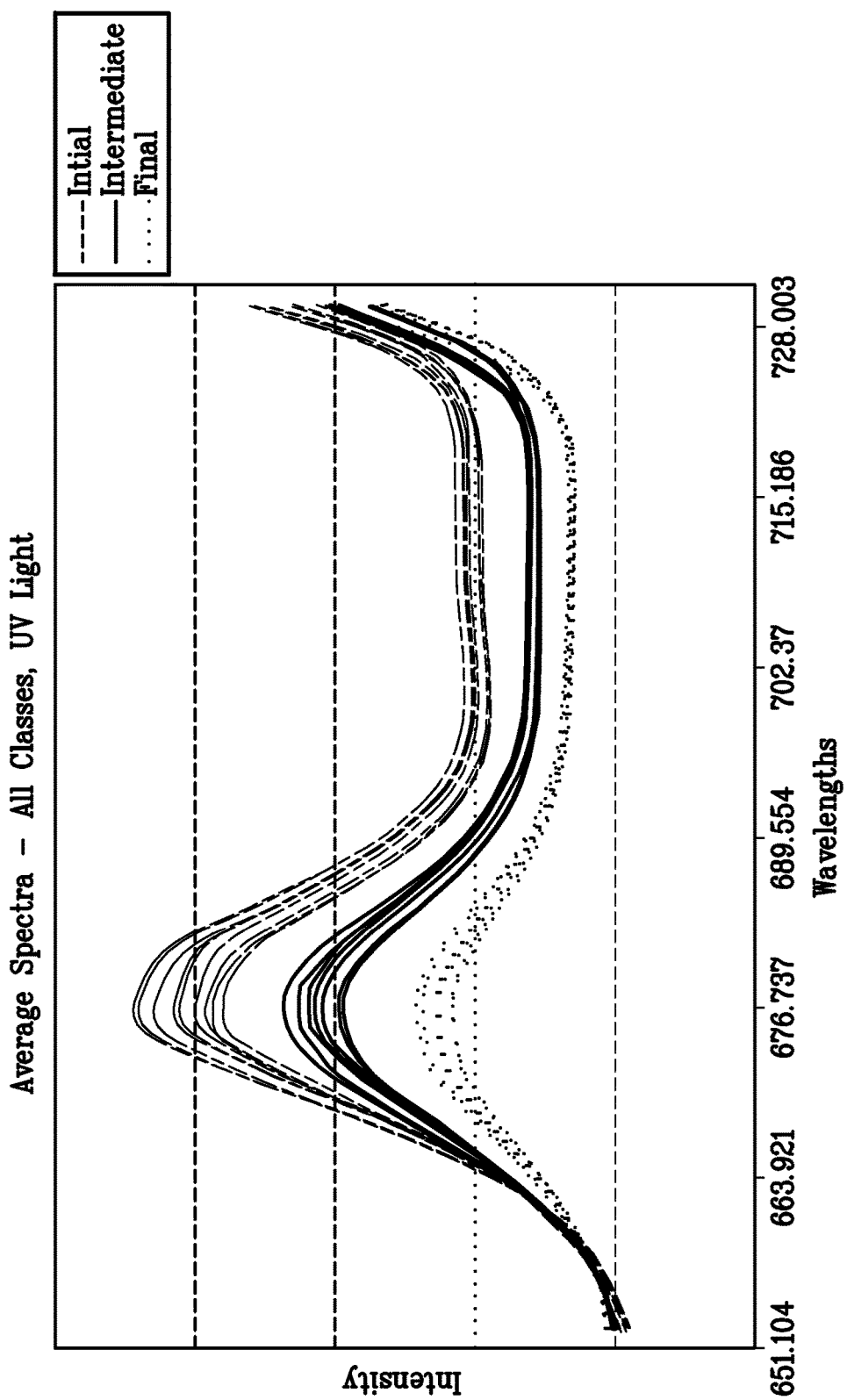
FIG. 8 presents a plot of intensity versus average spectra wavelength for multiple samples at three stages of processing for a hyperspectral imaging and analysis system using UV light, in accordance herewith.

Referring now to FIG. 8, a plot of intensity versus average spectra wavelength for tobacco samples at three different stages of processing is presented for a hyperspectral imaging and analysis system using UV light. Again, as may be seen, excellent resolution was achieved, with each stage of processing discernible from the others.

As may be appreciated, upon implementation in accordance with the foregoing teachings, the system will lessen or obviate the need to use sensorial panels in the quality control of commercially manufactured agricultural products.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

Illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. A method for monitoring a manufacturing process of an agricultural product, the method utilizing hyperspectral imaging and comprising: (a) scanning at least one region along a sample of agricultural product using at least one light source of a single or different wavelengths; (b) generating hyperspectral images from the at least one region; (c) determining a spectral fingerprint for the sample of agricultural product from the hyperspectral images; and (d) comparing the spectral fingerprint obtained in step (c) to a spectral fingerprint database containing a plurality of fingerprints obtained at various points of the manufacturing process, using a computer processor, to determine which point in the manufacturing process the sample has progressed to.

A2. The method of paragraph A1, further comprising: scanning multiple regions along the sample of agricultural product using at least one light source of a single or different wavelengths; and generating hyperspectral images from the multiple regions.

A3. The method of paragraph A1, further comprising determining a physicochemical code for the sample.

A4. The method of paragraph A1, wherein the manufacturing process produces an agricultural product with desirable sensory attributes.

A5. The method of paragraph A4, further comprising determining one or more features of a spectral fingerprint that correspond to the desirable sensory attributes.

A6. The method of paragraph A5, wherein the agricultural product is tobacco and the manufacturing process is a fermentation process.

A7. The method of paragraph A6, wherein the method determines the time required to complete the fermentation process for the tobacco sample.

A8. The method of paragraph A5, wherein the agricultural product is tobacco and the manufacturing process is a tobacco aging process.

A9. The method of paragraph A8, wherein the method determines the time required to complete the tobacco aging process for the tobacco sample.

A10. The method of paragraph A5, further comprising: correlating one or more features of the spectral fingerprint of the sample of the agricultural product to the desirable sensory attributes.

A11. The method of paragraph A1, wherein the at least one light source is positioned to minimize the angle of incidence of each beam of light with the sample.

A12. The method of paragraph A1, wherein manufacturing cost is a factor used by the computer processor in step (d).

A13. The method of paragraph A1, wherein the at least one light source for providing a beam of light comprises a light source selected from the group consisting of a tungsten light source, a halogen light source, a xenon light source, a mercury light source, an ultraviolet light source, and combinations thereof.

A14. The method of paragraph A1, further comprising repeating steps (a), (b), and (c) for a plurality of samples of agricultural product.

A15. The method of paragraph A14, further comprising, prior to step (d): storing data about the spectral fingerprints of the plurality of samples of agricultural product within a computer storage means; and storing at least a portion of at least some of the plurality of samples of agricultural product.

A16. A system for monitoring the manufacturing of an agricultural product, according to the method of paragraph A1.

B1. A method for determining the stage of processing for an agricultural product, the method utilizing hyperspectral imaging and comprising: (a) scanning multiple regions along a sample of a desirable agricultural product using at least one light source of different wavelengths; (b) generating hyperspectral images from the multiple regions; (c) forming a spectral fingerprint for the sample from the hyperspectral images; and (d) correlating the spectral fingerprint obtained in step (c) to a spectral fingerprint database containing a plurality of fingerprints obtained at various points of processing, using a computer processor, to determine the stage of processing.

B2. The method of paragraph B1, further comprising: (e) storing data about the spectral fingerprint within a computer storage means; and (f) repeating steps (a), (b), (c), and (d) using a plurality of samples.

B3. A system for determining the stage of processing for an agricultural product, according to the method of paragraph B2.

C1. A method of determining the stage of processing for a product, the method comprising: resolving whether a sample meets a desired attribute for the product and if so, applying hyperspectral imaging analysis and theoretic analysis to establish a relationship P comprising unique spectra of the sample, said unique spectra comprising at least two spectral elements x and y and values thereof; establishing through hyperspectral imaging analysis a characterization of the sample according to said spectral elements (at least x and y) of said unique spectra P; and mathematically resolving from said characterizations to determine whether the sample achieves the values of said spectral elements of P.

D1. A method for controlling a manufacturing process for producing an agricultural product, the method utilizing hyperspectral imaging and comprising: (a) obtaining a sample of agricultural product undergoing a manufacturing process, the manufacturing process conducted at one or more predetermined process parameters; (b) scanning at least one region along the sample of agricultural product using at least one light source of a single or different wavelengths; (c) generating hyperspectral images from the at least one region; (d) determining a spectral fingerprint for the sample of agricultural product from the hyperspectral images; (e) comparing the spectral fingerprint obtained in step (c) to a spectral fingerprint database containing a plurality of fingerprints obtained at various points of the manufacturing process, using a computer processor, to determine the stage of processing; and (e) adjusting at least one process parameter to optimize the manufacturing process.

D2. The method of paragraph D1, wherein the manufacturing process produces an agricultural product with desirable sensory attributes.

D3. The method of paragraph D2, further comprising determining one or more features of a spectral fingerprint that correspond to the desirable sensory attributes.

D4. The method of paragraph D1, wherein the agricultural product is tobacco and the manufacturing process is a fermentation process.

D5. The method of paragraph D4, wherein the method determines the time required to complete the fermentation process for the tobacco sample.

D6. The method of paragraph D1, wherein the agricultural product is tobacco and the manufacturing process is a tobacco aging process.

D7. The method of paragraph D6, wherein the method determines the time required to complete the tobacco aging process for the tobacco sample.

D8. The method paragraph D2, further comprising: correlating one or more features of the spectral fingerprint of the sample of the agricultural product to the desirable sensory attributes.

D9. The method of paragraph D1, wherein the at least one light source is positioned to minimize the angle of incidence of each beam of light with the sample.

D10. The method of paragraph D1, wherein manufacturing cost is a factor used by the computer processor in step (d).

E1. A method of creating a database for controlling a manufacturing process for producing an agricultural product, the method utilizing hyperspectral imaging and comprising: (a) obtaining a dark image and a reference image for calibration; (b) analyzing the reference image to obtain calibration coefficients; (c) obtaining a hyperspectral image for an agricultural sample; (d) removing dark values and normalizing the agricultural sample image; (e) applying calibration coefficients to compensate for fluctuations in system operating conditions; (f) repeating steps (c)-(e) for all agricultural samples; and (g) storing all hyperspectral sample hypercubes to form the database.

E2. A computer database stored in a computer readable medium, produced in accordance with paragraph E1.

INDUSTRIAL APPLICABILITY

The systems and methods disclosed herein are applicable to the tobacco industry and to other industries wherein agricultural products are selected and/or processed.

It is to be fully understood that certain aspects, characteristics, and features, of the forms disclosed herein, which are illustratively described and presented in the context or format of a plurality of separate forms, may also be illustratively described and presented in any suitable combination or sub-combination in the context or format of a single form. Conversely, various aspects, characteristics, and features, of the forms disclosed herein, which are illustratively described and presented in combination or sub-combination in the context or format of a single form, may also be illustratively described and presented in the context or format of a plurality of separate forms.

All patents, patent applications, and publications, cited or referred to in this specification are herein incorporated in their entirety by reference into the specification, to the same extent as if each individual patent, patent application, or publication, was specifically and individually indicated to be incorporated herein by reference. In addition, citation or identification of any reference in this specification shall not be construed or understood as an admission that such reference represents or corresponds to prior art. To the extent that section headings are used, they should not be construed as necessarily limiting.

While the forms disclosed herein have been described in connection with a number of exemplary forms, and implementations, the forms disclosed herein are not so limited, but rather cover various modifications, and equivalent arrangements, which fall within the purview of the present claims.

What is claimed:

1. A method for monitoring a manufacturing process of an agricultural product, the method utilizing hyperspectral imaging and comprising:
   (a) scanning at least one region along a sample of agricultural product using at least one light source of a single or different wavelengths;
   (b) generating hyperspectral images from the at least one region;
   (c) determining a spectral fingerprint for the sample of agricultural product from the hyperspectral images; and
   (d) comparing the spectral fingerprint obtained in step (c) to a spectral fingerprint database containing a plurality of fingerprints obtained at various points of the manufacturing process, using a computer processor, to determine to which point in the manufacturing process the sample has progressed.

2. The method of claim 1, further comprising:
   scanning multiple regions along the sample of agricultural product using at least one light source of a single or different wavelengths; and
   generating hyperspectral images from the multiple regions.

3. The method of claim 1, further comprising determining a physicochemical code for the sample.

4. The method of claim 1, wherein the manufacturing process produces an agricultural product with desirable sensory attributes.

5. The method of claim 4, further comprising determining one or more features of a spectral fingerprint that correspond to the desirable sensory attributes.

6. The method of claim 5, wherein the agricultural product is tobacco and the manufacturing process is a fermentation process.

7. The method of claim 6, wherein the method determines the time required to complete the fermentation process for the tobacco sample.

8. The method of claim 5, wherein the agricultural product is tobacco and the manufacturing process is a tobacco aging process.

9. The method of claim 8, wherein the method determines the time required to complete the tobacco aging process for the tobacco sample.

10. The method of claim 5, further comprising:
    correlating one or more features of the spectral fingerprint of the sample of the agricultural product to the desirable sensory attributes.

11. The method of claim 1, wherein the at least one light source is positioned to minimize the angle of incidence of each beam of light with the sample.

12. The method of claim 1, wherein the at least one light source for providing a beam of light comprises a light source selected from the group consisting of a tungsten light source, a halogen light source, a xenon light source, a mercury light source, an ultraviolet light source, and combinations thereof.

13. The method of claim 1, further comprising repeating steps (a), (b), and (c) for a plurality of samples of agricultural product.

14. The method of claim 13, further comprising, prior to step (d):
    storing data about the spectral fingerprints of the plurality of samples of agricultural product within a computer storage means.

15. A system for monitoring the manufacturing of an agricultural product, comprising a computer processor in communication with a hyperspectral imaging apparatus, the computer processor having a program stored on a computer-storage means within the computer processor, which program is executable to conduct the method according to claim 1.

16. A method for determining the stage of processing for an agricultural product, the method utilizing hyperspectral imaging and comprising:
    (a) scanning multiple regions along a sample of a desirable agricultural product using at least one light source of different wavelengths;

(b) generating hyperspectral images from the multiple regions;
(c) forming a spectral fingerprint for the sample from the hyperspectral images; and
(d) correlating the spectral fingerprint obtained in step (c) to a spectral fingerprint database containing a plurality of fingerprints obtained at various points of processing, using a computer processor, to determine the stage of processing.

17. The method of claim 16, further comprising:
(e) storing data about the spectral fingerprint within a computer storage means; and
(f) repeating steps (a), (b), (c), and (d) using a plurality of samples.

18. A system for determining the stage of processing for an agricultural product, comprising a computer processor in communication with a hyperspectral imaging apparatus, the computer processor having a program stored on a computer-storage means within the computer processor, which program is executable to conduct the method according to claim 17.

19. A method of determining the stage of processing for a product, the method comprising:
resolving whether a sample of a product meets a desired sensory attribute for the product and if so, applying hyperspectral imaging analysis and theoretic analysis to establish a relationship P comprising unique spectra of the sample, said unique spectra comprising at least two spectral elements x and y and values thereof;
establishing through hyperspectral imaging analysis a characterization of the sample according to said spectral elements (at least x and y) of said unique spectra P; and
mathematically resolving from said characterization to determine whether the sample achieves the values of said spectral elements of P to determine the progression of the sample through different stages of processing over time.

20. A method for controlling a manufacturing process for producing an agricultural product, the method utilizing hyperspectral imaging and comprising:
(a) obtaining a sample of agricultural product undergoing a manufacturing process, the manufacturing process conducted at one or more predetermined process parameters;
(b) scanning at least one region along the sample of agricultural product using at least one light source of a single or different wavelengths;
(c) generating hyperspectral images from the at least one region;
(d) determining a spectral fingerprint for the sample of agricultural product from the hyperspectral images;
(e) comparing the spectral fingerprint obtained in step (d) to a spectral fingerprint database containing a plurality of fingerprints obtained at various points of the manufacturing process, using a computer processor, to determine the stage of processing; and
(f) adjusting at least one process parameter to optimize the manufacturing process.

21. The method of claim 20, wherein the manufacturing process produces an agricultural product with desirable sensory attributes.

22. The method of claim 21, further comprising determining one or more features of a spectral fingerprint that correspond to the desirable sensory attributes.

23. The method claim 21, further comprising: correlating one or more features of the spectral fingerprint of the sample of the agricultural product to the desirable sensory attributes.

24. The method of claim 20, wherein the agricultural product is tobacco and the manufacturing process is a fermentation process.

25. The method of claim 24, wherein the method determines the time required to complete the fermentation process for the tobacco sample.

26. The method of claim 20, wherein the agricultural product is tobacco and the manufacturing process is a tobacco aging process.

27. The method of claim 26, wherein the method determines the time required to complete the tobacco aging process for the tobacco sample.

28. The method of claim 20, wherein the at least one light source is positioned to minimize the angle of incidence of each beam of light with the sample.

29. The method of claim 20, wherein manufacturing cost is a factor used in step (f).

30. A method of creating a database for controlling a manufacturing process for producing an agricultural product, the method utilizing hyperspectral imaging and comprising:
(a) obtaining a dark image and a reference image for calibration;
(b) analyzing the reference image to obtain calibration coefficients;
(c) obtaining a hyperspectral image for an agricultural sample;
(d) removing dark values and normalizing the agricultural sample image;
(e) applying calibration coefficients to compensate for fluctuations in system operating conditions;
(f) repeating steps (c)-(e) for all agricultural samples at different stages of processing over time;
(g) creating a plurality of hyperspectral sample hypercubes from said hyperspectral images and calibration coefficients obtained in step (f); and
(h) storing said hyperspectral sample hypercubes to form the database.

31. A computer database stored in a non-transitory computer readable medium, comprising:
a spectral fingerprint database of a plurality of hyperspectral images from one or more reference samples of desired agricultural products, obtained at different points in stages of processing;
one or more spectral fingerprints of a sample of an agricultural product being processed, obtained at one or more points in the stages of processing over time of said agricultural product being processed; and
said non-transitory medium further comprising code executable by a processor and configured to compare and/or correlate the spectral fingerprints of the agricultural products being processed with the spectral fingerprint database to determine the stage of processing over time of the agricultural products being processed.

* * * * *